US009512449B2

(12) United States Patent
Magnus

(10) Patent No.: US 9,512,449 B2
(45) Date of Patent: Dec. 6, 2016

(54) METHOD FOR PRODUCING PHENOL FROM RENEWABLE RESOURCES BY FERMENTATION

(71) Applicants: BAYER TECHNOLOGY SERVICES GMBH, Leverkusen (DE); BAYER MATERIALSCIENCE AG, Leverkusen (DE)

(72) Inventor: Jorgen Magnus, Düsseldorf (DE)

(73) Assignee: Covestro Deutschland AG, Leverkusen (DE)

(*) Notice: Subject to any disclaimer, the term of this patent is extended or adjusted under 35 U.S.C. 154(b) by 0 days.

(21) Appl. No.: 14/442,468

(22) PCT Filed: Nov. 13, 2013

(86) PCT No.: PCT/EP2013/073688
§ 371 (c)(1),
(2) Date: May 13, 2015

(87) PCT Pub. No.: WO2014/076113
PCT Pub. Date: May 22, 2014

(65) Prior Publication Data
US 2016/0273005 A1 Sep. 22, 2016

(30) Foreign Application Priority Data
Nov. 13, 2012 (EP) .................................... 12192342

(51) Int. Cl.
*C12N 9/88* (2006.01)
*C12P 7/22* (2006.01)
*C07K 14/245* (2006.01)
*C12N 9/90* (2006.01)
*C12N 15/52* (2006.01)

(52) U.S. Cl.
CPC ................ *C12P 7/22* (2013.01); *C07K 14/245* (2013.01); *C12N 9/88* (2013.01); *C12N 9/90* (2013.01); *C12N 15/52* (2013.01); *C12Y 401/01061* (2013.01); *C12Y 401/0304* (2013.01); *C12Y 402/01051* (2013.01); *C12Y 504/99005* (2013.01)

(58) Field of Classification Search
CPC ...................................................... C12N 9/88
USPC ..................... 435/156, 232, 252.3
See application file for complete search history.

(56) References Cited

U.S. PATENT DOCUMENTS

2004/0261147 A1* 12/2004 Meyer ................ C12N 15/8257
800/278
2009/0246835 A1 10/2009 Iwatani et al.
2013/0273624 A1 10/2013 Yukawa et al.

FOREIGN PATENT DOCUMENTS

EP         1602730 A2    12/2005
EP         2639295 A1    9/2013
WO    2012-063862 A1    5/2012

OTHER PUBLICATIONS

International Search Report dated Jan. 16, 2014, mailed Jan. 23, 2014.
Gibson, et al.; "Benzene-Free Synthesis of Phenol"; Angew. Chem. 2001, 113(10):1999-2002.
Wierckx et al.; "Engineering of solvent-tolerant Pseudomonas putida S12 for bioproduction of phenol from glucose"; Applied and Environmental Microbiology, Dec. 2005, vol. 71, No. 12, pp. 8221-8227.
Wierckx et al.; "Transcriptome analysis of a phenol-producing Pseudomonas putida S12 construct: genetic and physiological basis for improved production"; Journal of Bacteriology, 2008, vol. 190 (8), pp. 2822-2830.
Wierckx et al.; "Metabolic flux analysis of a phenol producing mutant of Pseudomonas putida S12: verification and complementation of hypotheses derived from transcriptomics", Journal of Biotechnology, 2009, vol. 143, pp. 124-129.
Wierckx, "Solvent-Tolerant Bioconversion" Construction and analysis of a phenol producing Pseudomonas putida S12. PhD-Thesis Technical University of Delft. 2009.
Meijnen et al., "Improved p-hydroxybenzoate production by engineered Pseudomonas putida S12 by using a mixed-substrate feeding strategy", Appl Microbiol Biotechnol. 2011. 90(3):885-893.
Barker, et al., "Microbial Synthesis of p-Hydroxybenzoic Acid from Glucose", Biotechnol Bioeng., 2001, 76 (4):376-90.
Sprenger, From scratch to value: engineering *Escherichia coli* wild type cells to the production of L-phenylalanine and other fine chemicals derived from chorismate. Appl Microbiol Biotechnol 2007. 75:739-749.
Bongaerts, et al., "Diversity-oriented production of metabolites derived from chorismate and their use in organic synthesis", Angew Chem Int Ed Engl. 2011. 50(34):7781-6.
Frost et al. "Biocatalytic Syntheses of aromatics from d-Glucose: Renewable Microbial Sources of Aromatic Compounds", Annu. Rev. Microbiol. 1995. 49:557-79.
Sprenger, "Aromatic Amino Acids", Microbiol Monogr. 2006. vol. 5. 93-127.
Boguslaw et al., "Properties of the reversible nonoxidative vanillate/4-hydroxybenzoate decarboxylase form Bacillus supstilis", Canadian Journal of Microbiology, Jan. 2008, vol. 54, No. 1, pp. 75-81, ISSN: 0008-4166.

* cited by examiner

*Primary Examiner* — Tekchand Saidha
(74) *Attorney, Agent, or Firm* — Drinker Biddle & Reath LLP

(57) ABSTRACT

The invention relates to a method of generating a recombinant host strain for producing phenol, comprising the steps of a) providing a host comprising chorismate, b) transforming the host with a first nucleic acid sequence comprising ubiC (SEQ ID NO: 1) encoding chorismate lyase that converts chorismate to 4-hydroxybenzoate, and c) transforming the host with a second nucleic acid sequence encoding an oxygen-tolerant 4-hydroxybenzoate decarboxylase that converts 4-hydroxybenzoate to phenol, thereby generating a recombinant host that is capable of producing phenol under aerobic conditions, wherein step b) and step c) are carried out simultaneously or sequentially. The invention also provides the recombinant host strain for producing phenol obtainable by the aforementioned method, as well as a method of producing phenol in the recombinant host strain.

22 Claims, 17 Drawing Sheets

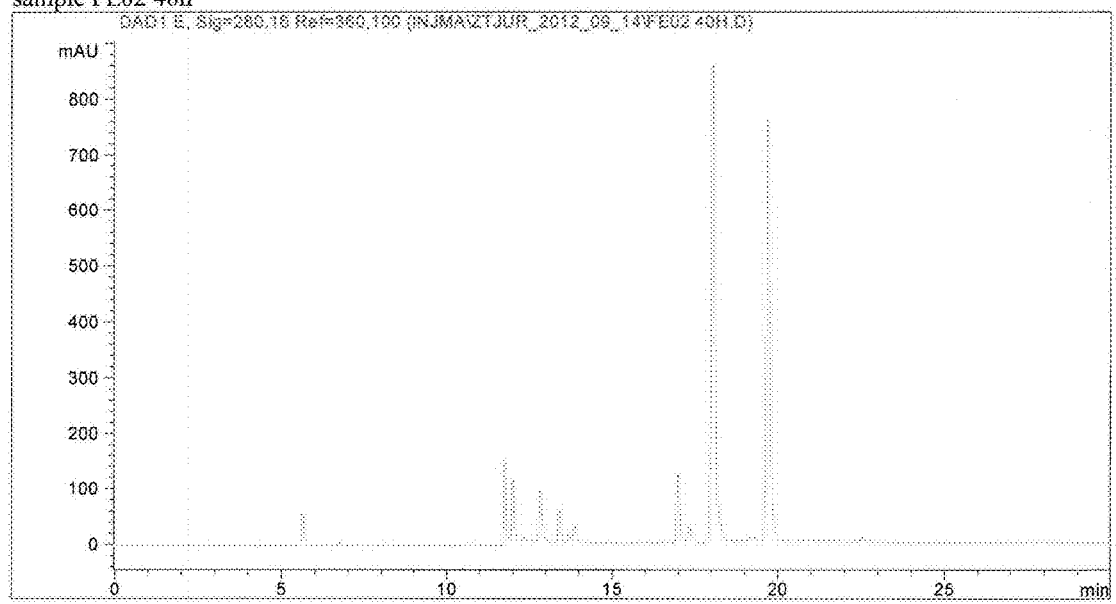

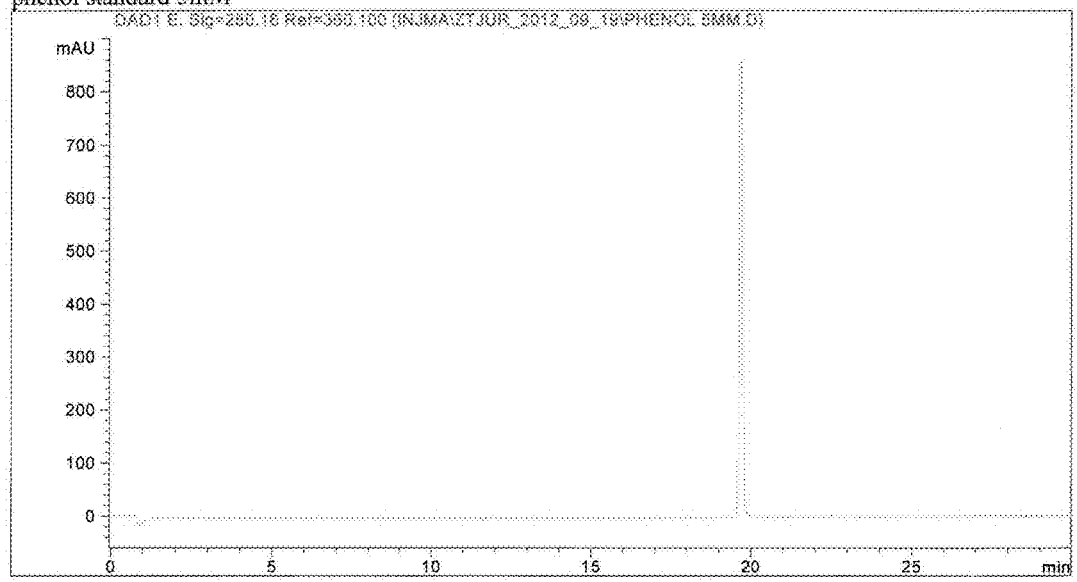

sample FE02 40h phenol standard 5 mM sample ubiC hbdBCD 24h phenol standard 1mM sample ubiC hbdBCD 24h phenol standard 1mM chromatogram sample aroLubiC hbdBCD, 24h phenol standard 1 mM UV Spectrum of phenol peak sample aroLubiC hbdBCD, 24h UV spectrum phenol standard 1 mM

FIG. 6A

*aroG*, SEQ ID NO:9
AGATCTCATATGAATTATCAGAACGACGATTTACGCATCAAAGAAATCAAAGAGTTACTTCCTC
CTGTCGCATTGCTGGAAAAATTCCCCGCTACTGAAAATGCCGCGAATACGGTTGCCCATGCCCG
AAAAGCGATCCATAAGATCCTGAAAGGTAATGATGATCGCCTGTTGGTTGTGATTGGCCCATGC
TCAATTCATGATCCTGTCGCGGCAAAAGAGTATGCCACTCGCTTGCTGGCGCTGCGTGAAGAGC
TGAAAGATGAGCTGGAAATCGTAATGCGCGTCTATTTTGAAAAGCCGCGTACCACGGTGGGCTG
GAAAGGGCTGATTAACGATCCGCACATGGATAATAGCTTCCAGATCAACGACGGTCTGCGTATA
GCCCGTAAATTGCTGCTTGATATTAACGACAGCGGTCTGCCAGCGGCAGGTGAGTTTCTCGATA
TGATCACCCCACAATATCTCGCTGACCTGATGAGCTGGGGCGCAATTGGCGCACGTACCACCGA
ATCGCAGGTGCACCGCGAACTGGCATCAGGGCTTTCTTGTCCGGTCGGCTTCAAAAATGGCACC
GACGGTACGATTAAAGTGGCTATCGATGCCATTAATGCCGCCGGTGCGCCGCACTGCTTCCTGT
CCGTAACGAAATGGGGCATTCGGCGATTGTGAATACCAGCGGTAACGGCGATTGCCATATCAT
TCTGCGCGGCGGTAAAGAGCCTAACTACAGCGCGAAGCACGTTGCTGAAGTGAAAGAAGGGCTG
AACAAAGCAGGCCTGCCAGCACAGGTGATGATCGATTTCAGCCATGCTAACTCGTCCAAACAAT
TCAAAAAGCAGATGGATGTTTGTGCTGACGTTTGCCAGCAGATTGCCGGTGGCGAAAAGGCCAT
TATTGGCGTGATGGTGGAAAGCCATCTGGTGGAAGGCAATCAGAGCCTCGAGAGCGGGGAGCCG
CTGGCCTACGGTAAGAGCATCACCGATGCCTGCATCGGCTGGGAAGATACCGATGCTCTGTTAC
GTCAACTGGCGAATGCAGTAAAAGCGCGTCGCGGGTAAGAAGGAGGATCC

FIG. 6B
*aroG^fbr*, SEQ ID NO:10
AGATCTCATATGAATTATCAGAACGACGATTTACGCATCAAAGAAATCAAAGAGTTACTTCCTC
CTGTCGCATTGCTGGAAAAATTCCCCGCTACTGAAAATGCCGCGAATACGGTTGCCCATGCCCG
AAAAGCGATCCATAAGATCCTGAAAGGTAATGATGATCGCCTGTTGGTTGTGATTGGCCCATGC
TCAATTCATGATCCTGTCGCGGCAAAAGAGTATGCCACTCGCTTGCTGGCGCTGCGTGAAGAGC
TGAAAGATGAGCTGGAAATCGTAATGCGCGTCTATTTTGAAAAGCCGCGTACCACGGTGGGCTG
GAAAGGGCTGATTAACGATCCGCACATGGATAATAGCTTCCAGATCAACGACGGTCTGCGTATA
GCCCGTAAATTGCTGCTTGATATTAACGACAGCGGTCTGCCAGCGGCAGGTGAGTTTCTCAATA
TGATCACCCCACAATATCTCGCTGACCTGATGAGCTGGGGCGCAATTGGCGCACGTACCACCGA
ATCGCAGGTGCACCGCGAACTGGCATCAGGGCTTTCTTGTCCGGTCGGCTTCAAAAATGGCACC
GACGGTACGATTAAAGTGGCTATCGATGCCATTAATGCCGCCGGTGCGCCGCACTGCTTCCTGT
CCGTAACGAAATGGGGCATTCGGCGATTGTGAATACCAGCGGTAACGGCGATTGCCATATCAT
TCTGCGCGGCGGTAAAGAGCCTAACTACAGCGCGAAGCACGTTGCTGAAGTGAAAGAAGGGCTG
AACAAAGCAGGCCTGCCAGCACAGGTGATGATCGATTTCAGCCATGCTAACTCGTCCAAACAAT
TCAAAAAGCAGATGGATGTTTGTGCTGACGTTTGCCAGCAGATTGCCGGTGGCGAAAAGGCCAT
TATTGGCGTGATGGTGGAAAGCCATCTGGTGGAAGGCAATCAGAGCCTCGAGAGCGGGGAGCCG
CTGGCCTACGGTAAGAGCATCACCGATGCCTGCATCGGCTGGGAAGATACCGATGCTCTGTTAC
GTCAACTGGCGAATGCAGTAAAAGCGCGTCGCGGGTAAGAAGGAGGATCC

FIG. 6C
*aroB*, SEQ ID NO: 11
<u>AGATCTCATATG</u>GAGAGGATTGTCGTTACTCTCGGGGAACGTAGTTACCCAATTACCATCGCAT
CTGGTTTGTTTAATGAACCAGCTTCATTCTTACCGCTGAAATCGGGCGAGCAGGTCATGTTGGT
CACCAACGAAACCCTGGCTCCTCTGTATCTCGATAAGGTCCGCGGCGTACTTGAACAGGCGGGT
GTTAACGTCGATAGCGTTATCCTCCCTGACGGCGAGCAGTATAAAAGCCTGGCTGTACTCGATA
CCGTCTTTACGGCGTTGTTACAAAAACCGCATGGTCGCGATACTACGCTGGTGGCGCTTGGCGG
CGGCGTAGTGGGCGATCTGACCGGCTTCGCGGCGGCGAGTTATCAGCGCGGTGTCCGTTTCATT
CAAGTCCCGACGACGTTACTGTCGCAGGTCGATTCCTCCGTTGGCGGCAAAACTGCGGTCAACC
ATCCCCTCGGTAAAAACATGATTGGCGCGTTCTACCAACCTGCTTCAGTGGTGGTGGATCTCGA
CTGTCTGAAAACGCTTCCCCGCGTGAGTTAGCGTCGGGGCTGGCAGAAGTCATCAAATACGGC
ATTATTCTTGACGGTGCGTTTTTTAACTGGCTGGAAGAGAATCTGGATGCGTTGTTGCGTCTGG
ACGGTCCGGCAATGGCGTACTGTATTCGCCGTTGTTGTGAACTGAAGGCAGAAGTTGTCGCCGC
CGACGAGCGCGAAACCGGGTTACGTGCTTTACTGAATCTGGGACACACCTTTGGTCATGCCATT
GAAGCTGAAATGGGGTATGGCAATTGGTTACATGGTGAAGCGGTCGCTGCGGGTATGGTGATGG
CGGCGCGGACGTCGGAACGTCTCGGGCAGTTTAGTTCTGCCGAAACGCAGCGTATTATAACCCT
GCTCAAGCGGGCTGGGTTACCGGTCAATGGGCCGCGCGAAATGTCCGCGCAGGCGTATTTACCG
CACATGCTGCGTGACAAGAAAGTCCTTGCGGGAGAGATGCGCTTAATTCTTCCGTTGGCAATTG
GTAAGAGTGAAGTTCGCAGCGGCGTTTCGCACGAGCTTGTTCTTAACGCCATTGCCGATTGTCA
ATCAGCGTAAGAAGGAGGATCC

FIG. 6D
*aroL*, SEQ ID NO: 12
<u>AGATCTCATATG</u>ACACAACCTCTTTTTCTGATCGGGCCTCGGGGCTGTGGTAAAACAACGGTCG
GAATGGCCCTTGCCGATTCGCTTAACCGTCGGTTTGTCGATACCGATCAGTGGTTGCAATCACA
GCTCAATATGACGGTCGCGGAGATCGTCGAAAGGGAAGAGTGGGCGGGATTTCGCGCCAGAGAA
ACGGCGGCGCTGGAAGCGGTAACTGCGCCATCCACCGTTATCGCTACAGGCGGCGGCATTATTC
TGACGGAATTTAATCGTCACTTCATGCAAAATAACGGGATCGTGGTTTATTTGTGTGCGCCAGT
ATCAGTCCTGGTTAACCGACTGCAAGCTGCACCGGAAGAAGATTTACGGCCAACCTTAACGGGA
AAACCGCTGAGCGAAGAAGTTCAGGAAGTGCTGGAAGAACGCGATGCGCTATATCGCGAAGTTG
CGCATATTATCATCGACGCAACAAACGAACCCAGCCAGGTGATTTCTGAAATTCGCAGCGCCCT
GGCACAGACGATCAATTGTTGAGAAGGAGGATCC

FIG. 6E
*ubiC*, SEQ ID NO:1
<u>AGATCTCATATG</u>TCACACCCCGCGTTAACGCAACTGCGTGCGCTGCGCTATTGTAAAGAGATCC
CTGCCCTAGATCCGCAACTGCTCGACTGGCTGTTGCTGGAGGATTCCATGACAAAACGTTTTGA
ACAGCAGGGAAAAACGGTAAGCGTGACGATGATCCGCGAAGGGTTTGTCGAGCAGAATGAAATC
CCCGAAGAACTGCCGCTGCTGCCGAAAGAGTCTCGTTACTGGTTACGTGAAATTTTGTTATGTG
CCGATGGTGAACCGTGGCTTGCCGGTCGTACCGTCGTTCCTGTGTCAACGTTAAGCGGGCCGGA
GCTGGCGTTACAAAAATTGGGTAAAACGCCGTTAGGACGCTATCTGTTCACATCATCGACATTA
ACCCGGGACTTTATTGAGATAGGCCGTGATGCCGGGCTGTGGGGCGACGTTCCCGCCTGCGAT
TAAGCGGTAAACCGCTGTTGCTAACAGAACTGTTTTTACCGGCGTCACCGTTGTAC<u>TAAGAAGG
AGGATCC</u>

FIG. 7

**Sequence of the gene complex *hbdBCD*** encoding 4-hydroxybenzoate decarboxylase as per SEQ ID NO: 2
Gene cluster: *hbdB*: 0.6 kbp, *hbdC*: 1.4 kbp, *hbdD*: 0.2 kbp ctgactaagccacgattttccattcttgccaacatttctgctaacgttgctttggtgctgacagctgcttctatcagtgccacctgttcgataccag
gtttatcagcaatggcgcgcatcaccgcgtactgtggtttggtcaggtcaggtaactcgtgctgccagcgagccgtgtgctgctgaaaaagc
tgtcgtaactgatggaacgctttatttcgtaacgccatgtaaactccgggctaattctctgtcgctatcatagcggttttttagtgacgaagaagat
gttgttacttttcaatccttgccgctgtggaaatgaaggagtatgttaataataacgttcgtatacgaacaattaagaggataagcaatgaaactg
atcgtcgggatgacagggcgctaccggtgcgcctcttggtgtggcattactgcaagcgctgcgggagatgccgaatgtcgagactcatctgg
tgatgtcgaagtgggcgaaaaccaccattgaactggaaacgccttacagcgctcgcgatgttgctgccctcgcagacttcagccataaccc
ggcggatcaggcggcgatcatctcatccggttcttttcgtaccgacggcatgatcgttattccgtgcagtatgaaaacgctcgccggtatccg
cgctggttacgccgatggcctggtagggcgcgcggcggacgtcgtgctcaaagaaggccgcaaactggtgctggtgccgcgtgaaatgc
cgcttagcaccatccatctcgaaaatatgctcgcactttcacgcatgggcgtggcgatggtgccgccgatgcctgccttttataaccatcccg
aaacggtagatgacattgtccaccatgtggtagcccgcgtgctggatcaatttggcctcgaacatccccacgccaggcgctggcaaggatt
gccgcaggcccggaattttctcaggagaatgaataatggcatttgatgatttacgcagcttttacaggcgcttgatgaccacggccagttac
tgaaaatcagcgaagaagtgaacgccgagccggatctggcagcagcagctaacgccaccgggcgtatcggcgacggcgcgcccgcgc
tgtggtttgataatattcgcggctttaccgatgcccgcgtggcgatgaacaccatcggttcctggcagaaccacgcgatttccctcggcctgc
cgccaaatgccccggttaaaaagcagattgatgagtttatccgccgctgggataacttcccgattgccccggagcgccgcgccaatccagc
ctgggcgcagaacaccgttgatggcgacgagatcaacctgttcgatatcctgccgctgtttcgtttaaacgatggcggtttctatctcgacaaa
gcgtgcgtggtttcccgcgatccgctcgacccggataacttcggcaagcagaacgtcggcatctaccgcatggaagtgaagggcaagcgt
aagctcggcctgcaaccggtgccgatgcacgatatcgccctgcatctgcataaagcagaagagcgcggtgaagatctgccgattgcgatc
acgctcggtaacgatccgatcatcacgctgatgggggccacgccgctgaaatatgatcagtccgagtacgaaatggcaggcgcgctgcgt
gaaagcccgtacccgatcgccaccgccccgttgaccggttttgatgtgccgtggggttcagaagtgatcctcgaaggggtcatcgaaagcc
gtaaacgcgaaatcgaagggccgttcggtgagtttaccgggcactactccggcgggcgtaacatgaccgtggtgcgcatcgataaagtct
cttaccgcaccaggccgattttcgaatcgctgtacctcggtatgccgtggaccgaaatcgactacctgatggggccagccacctgcgtgcc
gctgtatcagcagctgaaagccgagttccctgaagtgcaggcggtaaacgccatgtacacccatggcctgctggcgattatctccaccaaa
aaacgctacggcggctttgcccgcgcggtgggcctgcgcgcaatgaccacgccgcatggtctgggctacgtgaagatggtgattatggtc
gatgaagacgttgacccgttcaacctgccgcaggtgatgtgggcgctctcctcgaaagtgaacccggcaggggatttggtgcagttgccga
atatgtccgtgctggaactcgatccaggctcaagccctgcggggatcaccgacaagctgattatcgacgccactacgcctgtcgccccgga
caaccgtggtcactacagccaaccggtggtggatttaccggaaaccaaagcctgggctgaaaaactgaccgctatgctggctgcacgtaa
ataaggagaagaagATGATTTGTCCACGTTGTGCCGATGAACAGATTGAAGTGATGGCGAA
ATCGCCGGTGAAAGATGTCTGGACGGTATATCAGTGCCAGCATTGCCTTTATACCTG
GCGCGATACCGAACCGCTGCGCCGTACCAGCCGCGAACATTATCCCGAAGCGTTCC
GCATGACGCAGAAAGATATTGATGACGCGCCAATGGTGCCGAGCATCCCGCCGCTG
CTGGTGGAAGGTAAGCGTTAAataaaaggtccgatgccatcggaccttttattaaggtcaaattaccgcccatacgca
ccaggtaattaagaatccggtaaaaccgagaatggtcgttaacactgtccaggttttcagaccgtctgctaccgacaacccccagatatttggt
cacaatccagaaccctgagtcattaatatgtgacgcgccaagcccaccaaagcaggctgccagcgtcaccaatacgcactgaatcggattc
aa Fermentation pJF119ubiC pACYChbdBCD 90h phenol standard 1mM UV spectrum fermentation pJF119ubiC pACYChbdBCD 90h UV spectrum phenol standard 1 mM FIG. 9
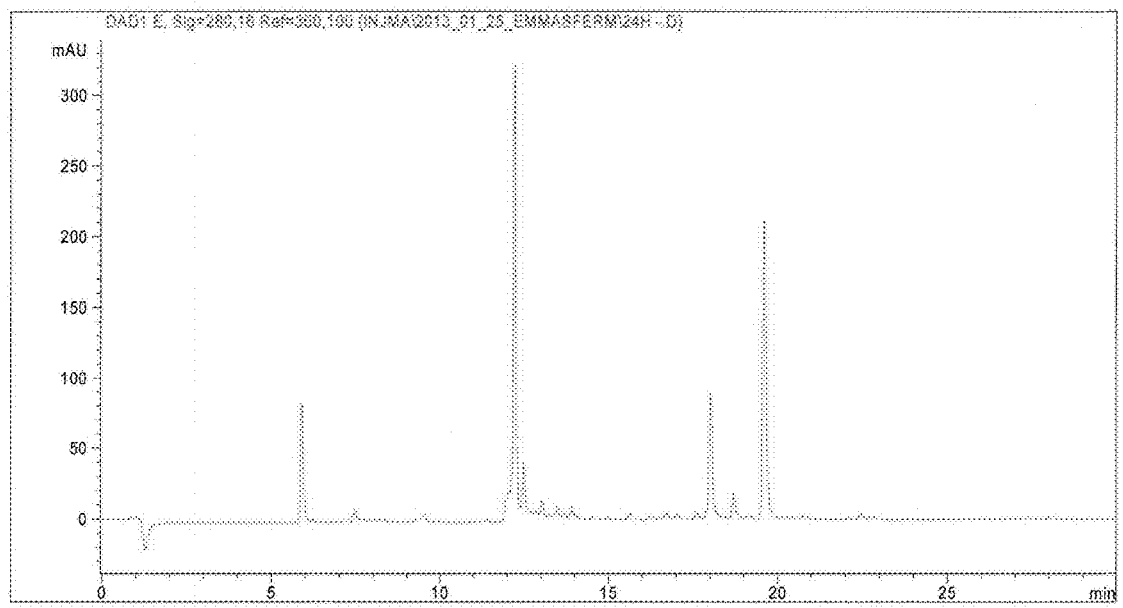
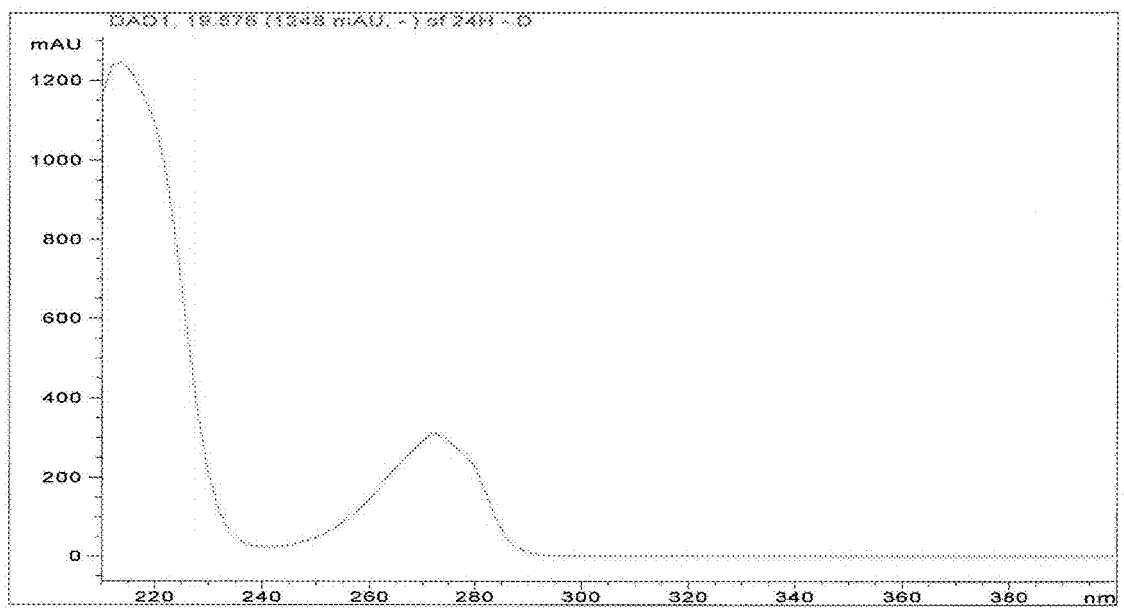

FIG. 10
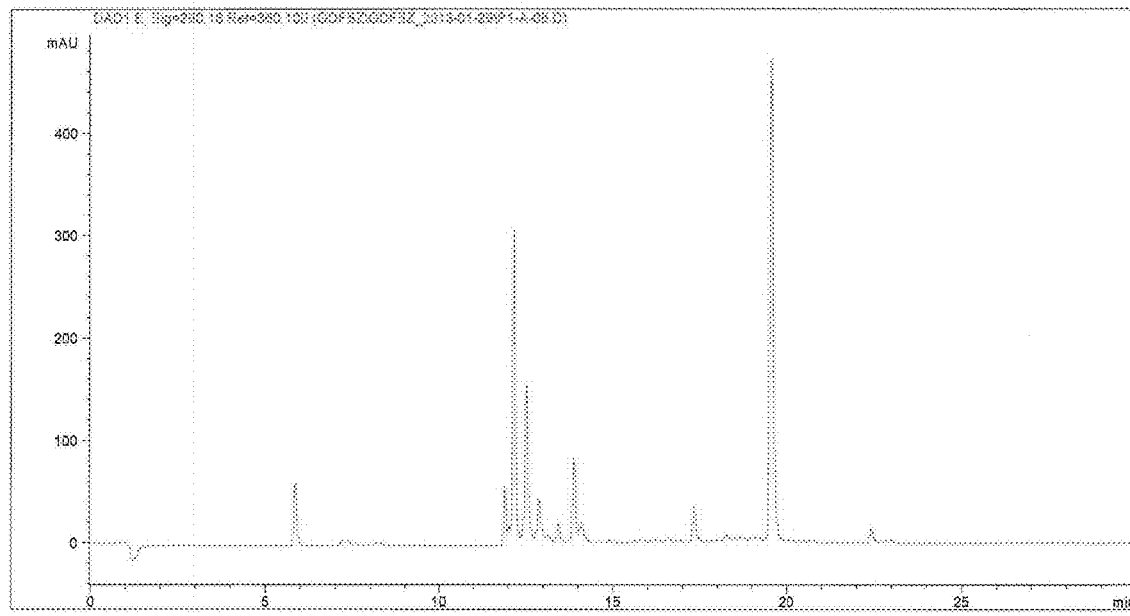
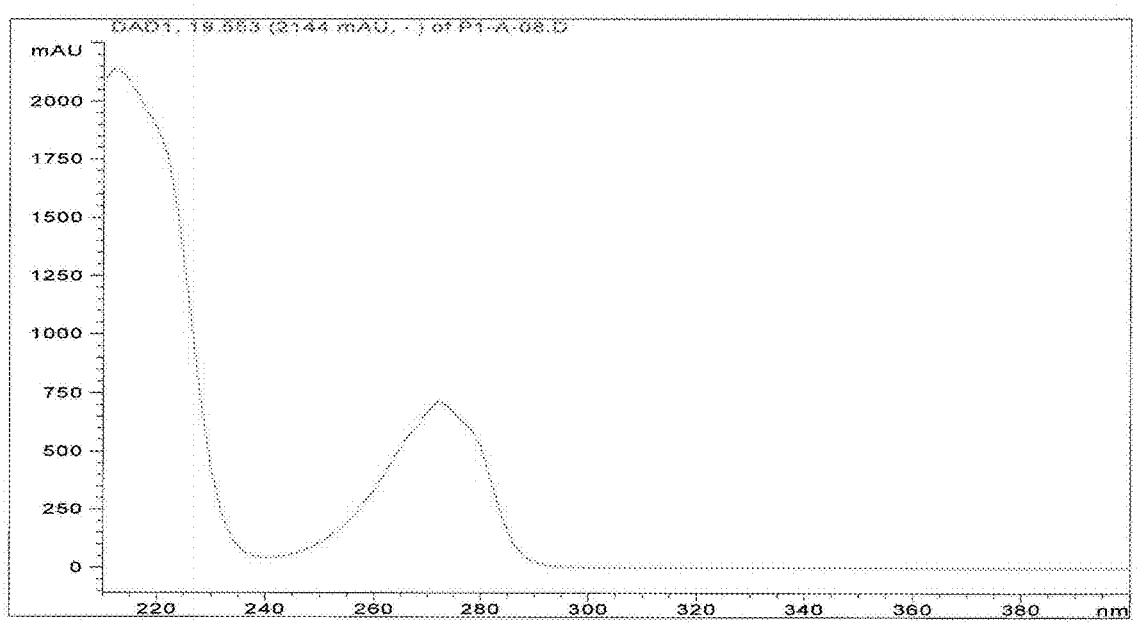

SEQUENCE LISTING

<160> NUMBER OF SEQ ID NOS: 18

<210> SEQ ID NO 1
<211> LENGTH: 519
<212> TYPE: DNA
<213> ORGANISM: Escherichia coli

<400> SEQUENCE: 1

```
agatctcata tgtcacaccc cgcgttaacg caactgcgtg cgctgcgcta ttgtaaagag      60
atccctgccc tagatccgca actgctcgac tggctgttgc tggaggattc catgacaaaa     120
cgttttgaac agcagggaaa aacggtaagc gtgacgatga tccgcgaagg gtttgtcgag     180
cagaatgaaa tccccgaaga actgccgctg ctgccgaaag agtctcgtta ctggttacgt     240
gaaattttgt tatgtgccga tggtgaaccg tggcttgccg gtcgtaccgt cgttcctgtg     300
tcaacgttaa gcgggccgga gctggcgtta caaaaattgg gtaaaacgcc gttaggacgc     360
tatctgttca catcatcgac attaacccgg gactttattg agataggccg tgatgccggg     420
ctgtgggggc gacgttcccg cctgcgatta agcggtaaac cgctgttgct aacagaactg     480 ttttttaccgg cgtcaccgtt gtactaagaa ggaggatcc                            519
```

<210> SEQ ID NO 2
<211> LENGTH: 2880
<212> TYPE: DNA
<213> ORGANISM: Escherichia coli

<400> SEQUENCE: 2

```
ctgactaagc cacgattttc cattcttgcc aacatttctg ctaacgttgc tttggtgctg    60
acagctgctt ctatcagtgc cacctgttcg ataccaggtt tatcagcaat ggcgcgcatc   120
accgcgtact gtggtttggt caggtcaggt aactcgtgct gccagcgagc cgtgtgctgc   180
tgaaaaagct gtcgtaactg atggaacgct ttatttcgta acgccatgta aactcccggc   240
taattctctg tcgctatcat agcggttttt tagtgacgaa gaagatgttg ttacttttca   300
atccttgccg ctgtggaaat gaaggagtat gttaataata cgttcgtat acgaacaatt    360
aagaggataa gcaatgaaac tgatcgtcgg gatgacaggg gctaccggtg cgcctcttgg   420
tgtggcatta ctgcaagcgc tgcgggagat gccgaatgtc gagactcatc tggtgatgtc   480
gaagtgggcg aaaaccacca ttgaactgga aacgccttac agcgctcgcg atgttgctgc   540
cctcgcagac ttcagccata acccggcgga tcaggcggcg atcatctcat ccggttcttt   600
tcgtaccgac ggcatgatcg ttattccgtg cagtatgaaa acgctcgccg gtatccgcgc   660
tggttacgcc gatggcctgg tagggcgcgc ggcggacgtc gtgctcaaag aaggccgcaa   720
actggtgctg gtgccgcgtg aaatgccgct tagcaccatc catctcgaaa atatgctcgc   780
actttcacgc atgggcgtgg cgatggtgcc gccgatgcct gccttttata accatcccga   840
aacggtagat gacattgtcc accatgtggt agcccgcgtg ctggatcaat tggcctcga    900
acatccccac gccaggcgct ggcaaggatt gccgcaggcc cggaattttt ctcaggagaa   960
tgaataatgg catttgatga tttacgcagc ttttttacagg cgcttgatga ccacggccag  1020
ttactgaaaa tcagcgaaga agtgaacgcc gagccggatc tggcagcagc agctaacgcc  1080
accgggcgta tcggcgacgg cgcgcccgcg ctgtggtttg ataatattcg cggctttacc  1140
gatgcccgcg tggcgatgaa caccatcggt tcctggcaga accacgcgat ttccctcggc  1200
ctgccgccaa atgccccggt taaaaagcag attgatgagt ttatccgccg ctgggataac  1260
ttcccgattg ccccggagcg ccgcgccaat ccagcctggg cgcagaacac cgttgatggc  1320
gacgagatca acctgttcga tatcctgccg ctgtttcgtt taaacgatgg cggtttctat  1380
ctcgacaaag cgtgcgtggt ttcccgcgat ccgctcgacc cggataactt cggcaagcag  1440
aacgtcggca tctaccgcat ggaagtgaag ggcaagcgta agctcggcct gcaaccggtg  1500
ccgatgcacg atatcgccct gcatctgcat aaagcagaag agcgcggtga agatctgccg  1560
attgcgatca cgctcggtaa cgatccgatc atcacgctga tggggccac gccgctgaaa  1620
tatgatcagt ccgagtacga aatggcaggc gcgctgcgtg aaagcccgta cccgatcgcc  1680
accgccccgt tgaccggttt tgatgtgccg tggggttcag aagtgatcct cgaagggtc   1740
atcgaaagcc gtaaacgcga aatcgaaggg ccgttcggtg agtttaccgg cactactcc   1800
ggcgggcgta acatgaccgt ggtgcgcatc gataaagtct cttaccgcac caggccgatt  1860
ttcgaatcgc tgtacctcgg tatgccgtgg accgaaatcg actacctgat ggggccagcc  1920
acctgcgtgc cgctgtatca gcagctgaaa gccgagttcc ctgaagtgca ggcggtaaac  1980
gccatgtaca cccatggcct gctggcgatt atctccacca aaaacgcta cggcggcttt   2040
gcccgcgcgg tgggcctgcg cgcaatgacc acgccgcatg gtctgggcta cgtgaagatg  2100
gtgattatgg tcgatgaaga cgttgacccg ttcaacctgc cgcaggtgat gtgggcgctc  2160
tcctcgaaag tgaacccggc aggggatttg gtgcagttgc cgaatatgtc cgtgctggaa  2220
ctcgatccag gctcaagccc tgcggggatc ccgacaagc tgattatcga cgccactacg   2280
cctgtcgccc cggacaaccg tggtcactac agccaaccgg tggtggattt accggaaacc  2340
```

```
aaagcctggg ctgaaaaact gaccgctatg ctggctgcac gtaaataagg agaagaagat    2400
gatttgtcca cgttgtgccg atgaacagat tgaagtgatg gcgaaatcgc cggtgaaaga    2460
tgtctggacg gtatatcagt gccagcattg cctttatacc tggcgcgata ccgaaccgct    2520
gcgccgtacc agccgcgaac attatcccga agcgttccgc atgacgcaga agatattga    2580
tgacgcgcca atggtgccga gcatcccgcc gctgctggtg aaggtaagc gttaaataaa     2640
aggtccgatg cccatcggac ctttttatta aggtcaaatt accgcccata cgcaccaggt    2700
aattaagaat ccggtaaaac cgagaatggt cgttaacact gtccaggttt tcagaccgtc    2760
tgctaccgac aaccccagat atttggtcac aatccagaac cctgagtcat taatatgtga    2820
cgcgccaagc ccaccaaagc aggctgccag cgtcaccaat acgcactgaa tcggattcaa    2880

<210> SEQ ID NO 3
<211> LENGTH: 1548
<212> TYPE: DNA
<213> ORGANISM: Escherichia coli

<400> SEQUENCE: 3
agcttgcatg cagattgcag cattacacgt cttgagcgat tgtgtaggct ggagctgctt      60
cgaagttcct atactttcta gagaatagga acttcggaat aggaacttca agatcccctc     120
acgctgccgc aagcactcag ggcgcaaggg ctgctaaagg aagcggaaca cgtagaaagc     180
cagtccgcag aaacggtgct gaccccggat gaatgtcagc tactgggcta tctggacaag     240
ggaaaacgca gcgcaaaga gaaagcaggt agcttgcagt gggcttacat ggcgatagct      300
agactgggcg gttttatgga cagcaagcga accggaattg ccagctgggg cgccctctgg     360
taaggttggg aagccctgca agtaaactg gatggctttc ttgccgccaa ggatctgatg      420
gcgcagggga tcaagatctg atcaagagac aggatgagga tcgtttcgca tgattgaaca     480
agatggattg cacgcaggtt ctccggccgc ttgggtggag aggctattcg gctatgactg     540
ggcacaacag acaatcggct gctctgatgc cgccgtgttc cggctgtcag cgcaggggcg     600
cccggttctt tttgtcaaga ccgacctgtc cggtgccctg aatgaactgc aggacgaggc     660
agcgcggcta tcgtggctgg ccacgacggg cgttccttgc gcagctgtgc tcgacgttgt     720
cactgaagcg ggaagggact ggctgctatt gggcgaagtg ccggggcagg atctcctgtc     780
atctcacctt gctcctgccg agaaagtatc catcatggct gatgcaatgc ggcggctgca     840
tacgcttgat ccggctacct gcccattcga ccaccaagcg aaacatcgca tcgagcgagc     900
acgtactcgg atggaagccg gtcttgtcga tcaggatgat ctggacgaag agcatcaggg     960
gctcgcgcca gccgaactgt tcgccaggct caaggcgcgc atgcccgacg gcgaggatct    1020
cgtcgtgacc catggcgatg cctgcttgcc gaatatcatg gtggaaaatg gccgcttttc    1080
tggattcatc gactgtggcc ggctgggtgt ggcggaccgc tatcaggaca tagcgttggc    1140
tacccgtgat attgctgaag agcttggcgg cgaatgggct gaccgcttcc tcgtgcttta    1200
cggtatcgcc gctcccgatt cgcagcgcat cgccttctat cgccttcttg acgagttctt    1260
ctgagcggga ctctggggtt cgaaatgacc gaccaagcga cgcccaacct gccatcacga    1320
gatttcgatt ccaccgccgc cttctatgaa aggttgggct tcggaatcgt tttccgggac    1380
gccggctgga tgatcctcca gcgcgggat ctcatgctgg agttcttcgc ccaccccagc     1440
ttcaaaagcg ctctgaagtt cctatacttt ctagagaata ggaacttcgg aataggaact    1500
aaggaggata ttcatatgga ccatggctaa ttcccatgtc agccgtta                  1548
```

<210> SEQ ID NO 4
<211> LENGTH: 1084
<212> TYPE: DNA
<213> ORGANISM: Escherichia coli

<400> SEQUENCE: 4

```
agcttaacgg ctgacatggg aattagccat ggtccatatg aatatcctcc ttagttccta      60
ttccgaagtt cctattctct agaaagtata ggaacttcgg cgcgcctacc tgtgacggaa     120
gatcacttcg cagaataaat aaatcctggt gtccctgttg ataccgggaa gccctgggcc     180
aactttggc gaaaatgaga cgttgatcgg cacgtaagag gttccaactt tcaccataat      240
gaataagat cactaccggg cgtatttttt gagttgtcga gattttcagg agctaaggaa      300
gctaaaatgg agaaaaaaat cactggatat accaccgttg atatatccca atggcatcgt     360
aaagaacatt ttgaggcatt tcagtcagtt gctcaatgta cctataacca gaccgttcag     420
ctggatatta cggcctttttt aaagaccgta agaaaaata agcacaagtt ttatccggcc     480
tttattcaca ttcttgcccg cctgatgaat gctcatccgg aattacgtat ggcaatgaaa     540
gacggtgagc ggtgatatgg gatagtgttc acccttgtta caccgtttc catgagcaaa      600
ctgaaacgtt ttcatcgctc tggagtgaat accacgacga tttccggcag tttctacaca     660
tatattcgca agatgtggcg tgttacggtg aaaacctggc ctatttccct aaagggttta     720
ttgagaatat gttttttcgtc tcagccaatc cctgggtgag tttcaccagt tttgatttaa     780
acgtggccaa tatggacaac ttcttcgccc ccgttttcac catgggcaaa tattatacgc     840
aaggcgacaa ggtgctgatg ccgctggcga ttcaggttca tcatgccgtt tgtgatggct     900
tccatgtcgg cagatgctta atgaatacaa cagtactgcg atgagtggca gggcggggcg     960
taaggcgcgc catttaaatg aagttcctat tccgaagttc ctattctcta gaaagtatag    1020
gaacttcgaa gcagctccag cctacacaat cgctcaagac gtgtaatgct gcaatctgca    1080
tgca                                                                 1084
```

<210> SEQ ID NO 5
<211> LENGTH: 70
<212> TYPE: DNA
<213> ORGANISM: Artificial Sequence
<220> FEATURE:
<223> OTHER INFORMATION: 5' primer

<400> SEQUENCE: 5

```
cccatgcgtc tggaagtctt ttgtgaagac cgactcggtc tgacccgcga gtgtaggctg      60
gagctgcttc                                                            70
```

<210> SEQ ID NO 6
<211> LENGTH: 73
<212> TYPE: DNA
<213> ORGANISM: Artificial Sequence
<220> FEATURE:
<223> OTHER INFORMATION: 3' primer

<400> SEQUENCE: 6

```
ctcttcgttc ttcttctgac tcagaccata ttcccgcaac ttattggcaa tcccatatga      60
atatcctcct tag                                                        73
```

<210> SEQ ID NO 7
<211> LENGTH: 72
<212> TYPE: DNA
<213> ORGANISM: Artificial Sequence
<220> FEATURE:

<223> OTHER INFORMATION: 5' primer

<400> SEQUENCE: 7

| gaggtttatt atggttgctg aattgaccgc attacgcgat caaattgatg accatatgaa | 60 |
| tatcctcctt ag | 72 |

<210> SEQ ID NO 8
<211> LENGTH: 71
<212> TYPE: DNA
<213> ORGANISM: Artificial Sequence
<220> FEATURE:
<223> OTHER INFORMATION: 3' primer

<400> SEQUENCE: 8

| gaagaagttg aagaagagta gtcctttata ttgagtgtat cgccaacgcg cgtgtaggct | 60 |
| ggagctgctt c | 71 |

<210> SEQ ID NO 9
<211> LENGTH: 1074
<212> TYPE: DNA
<213> ORGANISM: Escherichia coli

<400> SEQUENCE: 9

| agatctcata tgaattatca gaacgacgat ttacgcatca agaaatcaa agagttactt | 60 |
| cctcctgtcg cattgctgga aaaattcccc gctactgaaa atgccgcgaa tacggttgcc | 120 |
| catgcccgaa aagcgatcca taagatcctg aaaggtaatg atgatcgcct gttggttgtg | 180 |
| attggcccat gctcaattca tgatcctgtc gcggcaaaag agtatgccac tcgcttgctg | 240 |
| gcgctgcgtg aagagctgaa agatgagctg gaaatcgtaa tgcgcgtcta ttttgaaaag | 300 |
| ccgcgtacca cggtgggctg gaaagggctg attaacgatc cgcacatgga taatagcttc | 360 |
| cagatcaacg acggtctgcg tatagcccgt aaattgctgc ttgatattaa cgacagcggt | 420 |
| ctgccagcgg caggtgagtt tctcgatatg atcaccccac aatatctcgc tgacctgatg | 480 |
| agctggggcg caattggcgc acgtaccacc gaatcgcagg tgcaccgcga actggcatca | 540 |
| gggctttctt gtccggtcgg cttcaaaaat ggcaccgacg gtacgattaa agtggctatc | 600 |
| gatgccatta atgccgccgg tgcgccgcac tgcttcctgt ccgtaacgaa atgggggcat | 660 |
| tcggcgattg tgaataccag cggtaacggc gattgccata tcattctgcg cggcggtaaa | 720 |
| gagcctaact acagcgcgaa gcacgttgct gaagtgaaag aagggctgaa caaagcaggc | 780 |
| ctgccagcac aggtgatgat cgatttcagc catgctaact cgtccaaaca attcaaaaag | 840 |
| cagatggatg tttgtgctga cgtttgccag cagattgccg gtggcgaaaa ggccattatt | 900 |
| ggcgtgatgg tggaaagcca tctggtggaa ggcaatcaga gcctcgagag cggggagccg | 960 |
| ctggcctacg gtaagagcat caccgatgcc tgcatcggct gggaagatac cgatgctctg | 1020 |
| ttacgtcaac tggcgaatgc agtaaaagcg cgtcgcgggt aagaaggagg atcc | 1074 |

<210> SEQ ID NO 10
<211> LENGTH: 1074
<212> TYPE: DNA
<213> ORGANISM: Escherichia coli

<400> SEQUENCE: 10

| agatctcata tgaattatca gaacgacgat ttacgcatca agaaatcaa agagttactt | 60 |
| cctcctgtcg cattgctgga aaaattcccc gctactgaaa atgccgcgaa tacggttgcc | 120 |
| catgcccgaa aagcgatcca taagatcctg aaaggtaatg atgatcgcct gttggttgtg | 180 |

```
attggcccat gctcaattca tgatcctgtc gcggcaaaag agtatgccac tcgcttgctg      240
gcgctgcgtg aagagctgaa agatgagctg gaaatcgtaa tgcgcgtcta ttttgaaaag      300
ccgcgtacca cggtgggctg gaaagggctg attaacgatc cgcacatgga taatagcttc      360
cagatcaacg acggtctgcg tatagcccgt aaattgctgc ttgatattaa cgacagcggt      420
ctgccagcgg caggtgagtt tctcaatatg atcaccccac aatatctcgc tgacctgatg      480
agctggggcg caattggcgc acgtaccacc gaatcgcagg tgcaccgcga actggcatca      540
gggctttctt gtccggtcgg cttcaaaaat ggcaccgacg gtacgattaa agtggctatc      600
gatgccatta tgccgccggt gcgccgcac tgcttcctgt ccgtaacgaa atgggggcat       660
tcggcgattg tgaataccag cggtaacggc gattgccata tcattctgcg cggcggtaaa      720
gagcctaact acagcgcgaa gcacgttgct gaagtgaaag aagggctgaa caaagcaggc      780
ctgccagcac aggtgatgat cgatttcagc catgctaact cgtccaaaca attcaaaaag      840
cagatggatg tttgtgctga cgtttgccag cagattgccg gtggcgaaaa ggccattatt      900
ggcgtgatgg tggaaagcca tctggtggaa ggcaatcaga gcctcgagag cggggagccg      960
ctggcctacg gtaagagcat caccgatgcc tgcatcggct gggaagatac cgatgctctg     1020
ttacgtcaac tggcgaatgc agtaaaagcg cgtcgcgggt aagaaggagg atcc           1074

<210> SEQ ID NO 11
<211> LENGTH: 1110
<212> TYPE: DNA
<213> ORGANISM: Escherichia coli

<400> SEQUENCE: 11
agatctcata tggagaggat tgtcgttact ctcggggaac gtagttaccc aattaccatc       60
gcatctggtt tgtttaatga accagcttca ttcttaccgc tgaaatcggg cgagcaggtc      120
atgttggtca ccaacgaaac cctggctcct ctgtatctcg ataaggtccg cggcgtactt      180
gaacaggcgg gtgttaacgt cgatagcgtt atcctccctg acggcgagca gtataaaagc      240
ctggctgtac tcgataccgt ctttacggcg ttgttacaaa aaccgcatgg tcgcgatact      300
acgctggtgg cgcttggcgg cggcgtagtg gcgatctga ccggcttcgc ggcggcgagt       360
tatcagcgcg gtgtccgttt cattcaagtc ccgacgacgt tactgtcgca ggtcgattcc      420
tccgttggcg gcaaaactgc ggtcaaccat cccctcggta aaacatgat tggcgcgttc       480 taccaacctg cttcagtggt ggtggatctc gactgtctga aaacgcttcc cccgcgtgag      540
ttagcgtcgg ggctggcaga agtcatcaaa tacggcatta ttcttgacgg tgcgtttttt      600
aactggctgg aagagaatct ggatgcgttg ttgcgtctgg acggtccggc aatggcgtac      660
tgtattcgcc gttgttgtga actgaaggca gaagttgtcg ccgccgacga gcgcgaaacc      720
gggttacgtg ctttactgaa tctgggacac acctttggtc atgccattga agctgaaatg      780
gggtatggca attggttaca tgtgaagcg tcgctgcgg gtatggtgat ggcggcgcgg        840
acgtcggaac gtctcgggca gtttagttct gccgaaacgc agcgtattat aaccctgctc      900
aagcgggctg ggttaccggt caatgggccg cgcgaaatgt ccgcgcaggc gtatttaccg      960
cacatgctgc gtgacaagaa agtccttgcg ggagagatgc gcttaattct tccgttggca     1020
attggtaaga gtgaagttcg cagcggcgtt tcgcacgagc ttgttcttaa cgccattgcc     1080
gattgtcaat cagcgtaaga aggaggatcc                                     1110

<210> SEQ ID NO 12
```

```
<211> LENGTH: 546
<212> TYPE: DNA
<213> ORGANISM: Escherichia coli

<400> SEQUENCE: 12
agatctcata tgacacaacc tcttttctg atcgggcctc ggggctgtgg taaaacaacg      60
gtcggaatgg cccttgccga ttcgcttaac cgtcggtttg tcgataccga tcagtggttg     120
caatcacagc tcaatatgac ggtcgcggag atcgtcgaaa gggaagagtg ggcgggattt     180
cgcgccagag aaacggcggc gctggaagcg gtaactgcgc catccaccgt tatcgctaca     240
ggcggcggca ttattctgac ggaatttaat cgtcacttca tgcaaaataa cgggatcgtg     300
gtttatttgt gtgcgccagt atcagtcctg gttaaccgac tgcaagctgc accggaagaa     360
gatttacggc caaccttaac gggaaaaccg ctgagcgaag aagttcagga agtgctggaa     420
gaacgcgatg cgctatatcg cgaagttgcg catattatca tcgacgcaac aaacgaaccc     480
agccaggtga tttctgaaat tcgcagcgcc ctggcacaga cgatcaattg ttgagaagga     540
ggatcc                                                               546

<210> SEQ ID NO 13
<211> LENGTH: 3965
<212> TYPE: DNA
<213> ORGANISM: Artificial Sequence
<220> FEATURE:
<223> OTHER INFORMATION: Artificial Sequence

<400> SEQUENCE: 13
tcaaggcgca ctcccgttct ggataatgtt ttttgcgccg acatcataac ggttctggca      60
aatattctga atgagctgt tgacaattaa tcatcggctc gtataatgtg tggaattgtg     120
agcggataac aatttcacac aggaaacaga attcccctct agaataatt ttgtttaact     180 ttaagaagga gatatacata tggaacgtat tgttgttacc ctgggtgaac gtagctatcc     240
gattaccatt gcaagcggtc tgtttaatga accggcaagc tttctgccgc tgaaaagcgg     300
tgaacaggtt atgctggtta ccaatgaaac cctggcaccg ctgtatctgg ataaagttcg     360
tggtgttctg gaacaggcag gcgttaatgt tgatagcgtt attctgccgg atggcgaaca     420
gtataaaagc ctggcagttc tggataccgt ttttaccgca ctgctgcaga accgcatgg     480 tcgtgatacc ccctggttg cactgggtgg tggtgttgtt ggtgatctga ccggttttgc     540
agccgcaagc tatcagcgtg gtgtgcgttt tattcaggtt ccgaccaccc tgctgagcca     600
ggttgatagc agcgttggtg gtaaaaccgc agtaatcat ccgctgggca aaaatatgat     660
tggtgcattt tatcagcctg ccagcgttgt tgtggatctg gattgtctga aaccctgcc     720 tccgcgtgaa ctggccagcg gtctggccga agttatcaaa tatggtatta ttctggatgg     780
tgccttcttc aattggctgg aagaaaatct ggatgccctg ctgcgcctgg atggtccggc     840
aatggcatat tgtattcgtc gttgttgcga actgaaagcc gaagttgttg cagcagatga     900
acgtgaaacc ggtctgcgtg cactgctgaa tctgggtcat acctttggtc atgcaattga     960
agcagaaatg ggttatggta attggctgca tggtgaagca gttgcagccg gtatggttat    1020
ggcagcacgt accagcgaac gtctgggtca gtttagcagc gcagaaaccc agcgtattat    1080
cacgctgctg aaacgtgcag gtctgccggt taatggtcct cgtgaaatga gcgcacaggc    1140
atatctgccg cacatgctgc gtgataaaaa agttctggca ggcgaaatgc gtctgatcct    1200
gccgctggca attggtaaaa gcgaagttcg tagcggtgtt agccatgaac tggttctgaa    1260
tgcaattgcc gattgtcaga gcgcataaga aggaggatct catatgaact atcagaacga    1320
```

```
tgacctgcgc atcaaagaaa ttaaagaact gctgcctccg gttgcactgc tggaaaaatt    1380
tccggcaacc gaaaatgcag caaataccgt tgcacatgca cgtaaagcca ttcacaaaat    1440
tctgaaaggt aatgatgatc gcctgctggt tgttattggt ccgtgtagca ttcatgatcc    1500
ggttgccgca aaagaatatg caacccgtct gctggcactg cgtgaagaac tgaaagatga    1560
actggaaatt gtgatgcgcg tgtattttga aaaccgcgt accaccgttg gttggaaagg    1620
tctgattaat gatccgcaca tggataacag ctttcagatt aacgatggtc tgcgtattgc    1680
ccgtaaactg ctgctggata ttaatgatag cggtctgcct gcagccggtg aatttctgaa    1740
tatgattaca ccgcagtatc tggccgatct gatgagctgg ggtgcaattg gtgcacgcac    1800
caccgaaagc caggttcatc gtgaactggc aagcggtctg agctgtccgg ttggctttaa    1860
aaacggcacc gatggcacca ttaaagttgc aattgatgca attaatgcag cgggtgcacc    1920
gcattgtttt ctgagcgtta ccaaatgggg tcatagcgca attgttaata ccagcggtaa    1980
tggtgattgc catattattc tgcgtggtgg taaagaaccg aattattcag caaaacatgt    2040
ggccgaagtt aaagaaggtc tgaataaagc aggtctgcca gcacaggtta tgattgattt    2100
tagccatgca aatagcagca aacagttcaa aaaacaaatg gatgtttgtg ccgatgtgtg    2160
tcagcagatt gccggtggtg aaaaagcaat tattggtgtt atggttgaaa gccatctggt    2220
ggaaggtaat cagagcctgg aaagcggtga accgctggcc tatggtaaaa gcattaccga    2280
tgcatgtatt ggttgggaag ataccgatgc cctgctgcgt cagctggcaa atgcagttaa    2340
agcacgtcgt ggttaagaag gaggatcctc tagagtcgac ctgcaggcat gcaagcttaa    2400
cggctgacat gggaattagc catggtccat atgaatatcc tccttagttc ctattccgaa    2460
gttcctattc tctagaaagt ataggaactt cggcgcgcct acctgtgacg gaagatcact    2520
tcgcagaata aataaatcct ggtgtccctg ttgataccgg gaagccctgg gccaactttt    2580
ggcgaaaatg agacgttgat cggcacgtaa gaggttccaa cttttcaccat aatgaaataa    2640 gatcactacc gggcgtattt tttgagttgt cgagattttc aggagctaag gaagctaaaa    2700
tggagaaaaa aatcactgga tataccaccg ttgatatatc ccaatggcat cgtaaagaac    2760
attttgaggc atttcagtca gttgctcaat gtacctataa ccagaccgtt cagctggata    2820
ttacggcctt tttaaagacc gtaaagaaaa ataagcacaa gttttatccg gcctttattc    2880
acattcttgc ccgcctgatg aatgctcatc cggaattacg tatggcaatg aaagacggtg    2940
agctggtgat atgggatagt gttcacccct tgttacaccgt tttccatgag caaactgaaa    3000
cgttttcatc gctctggagt gaataccacg acgatttccg gcagtttcta cacatatatt    3060
cgcaagatgt ggcgtgttac ggtgaaaacc tggcctattt ccctaaaggg tttattgaga    3120
atatgttttt cgtctcagcc aatccctggg tgagtttcac cagttttgat ttaaacgtgg    3180
ccaatatgga caacttcttc gcccccgttt tcaccatggg caaatattat acgcaaggcg    3240
acaaggtgct gatgccgctg gcgattcagg ttcatcatgc cgtttgtgat ggcttccatg    3300
tcggcagatg cttaatgaat acaacagtac tgcgatgagt ggcagggcgg ggcgtaaggc    3360
gcgccattta aatgaagttc ctattccgaa gttcctattc tctagaaagt ataggaactt    3420
cgaagcagct ccagcctaca caatcgctca agacgtgtaa tgctgcaatc tgcatgcaag    3480
cttctgtttt ggcggatgag agaagatttt cagcctgata cagattaaat cagaacgcag    3540
aagcggtctg ataaaacaga atttgcctgg cggcagtagc gcggtggtcc cacctgaccc    3600
catgccgaac tcagaagtga aacgccgtag cgccgatggt agtgtggggt ctccccatgc    3660
```

| | |
|---|---:|
| gagagtaggg aactgccagg catcaaataa aacgaaaggc tcagtcgaaa gactgggcct | 3720 |
| ttcgttttat ctgttgtttg tcggtgaacg ctctcctgag taggacaaat ccgccgggag | 3780 |
| cggatttgaa cgttgcgaag caacggcccg gagggtggcg ggcaggacgc ccgccataaa | 3840 |
| ctgccaggca tcaaattaag cagaaggcca tcctgacgga tggccttttt gcgtttctac | 3900 |
| aaactctttt gtttattttt ctaaatacat tcaaatatgt atccgctcat gagacaataa | 3960 |
| ccctg | 3965 |

<210> SEQ ID NO 14
<211> LENGTH: 81
<212> TYPE: DNA
<213> ORGANISM: Artificial Sequence
<220> FEATURE:
<223> OTHER INFORMATION: Artificial Sequence

<400> SEQUENCE: 14

| | |
|---|---:|
| tgctgtgctc actgttttt ctttgggcgg tagccaataa ccttaacgac attttattat | 60 |
| caaggcgcac tcccgttctg g | 81 |

<210> SEQ ID NO 15
<211> LENGTH: 79
<212> TYPE: DNA
<213> ORGANISM: Artificial Sequence
<220> FEATURE:
<223> OTHER INFORMATION: Artificial Sequence

<400> SEQUENCE: 15

| | |
|---|---:|
| cagcatggag gcgagagtga taaagtctgc gccaacgtgg ccgatggtca gaaccccag | 60 |
| ggttattgtc tcatgagcg | 79 |

<210> SEQ ID NO 16
<211> LENGTH: 12496
<212> TYPE: DNA
<213> ORGANISM: Artificial Sequence
<220> FEATURE:
<223> OTHER INFORMATION: Artificial Sequence

<400> SEQUENCE: 16

| | |
|---|---:|
| tgcgtggtaa aggtaagtct atcgaaatca acaagctgaa ccgtatcact gcgctgttca | 60 |
| tgctggtaac gacctggatt gttgccaccc tgaacccgag catcctgggt atgattgaaa | 120 |
| ccctgggcgg tccaatcatc gcgatgatcc tgttcctgat gccgatgtac gcaattcaga | 180 |
| aagtaccggc aatgcgtaag tacagcggtc acatcagcaa cgtattcgtt gtcgtgatgg | 240 |
| gtctgattgc aatctccgca atcttctact ctctgttcag ctaagtcctt tcgcgccgct | 300 |
| ttcgggcggc gcttcctccg tttaacgcg atgtatttcc tatgattagc gtattcgata | 360 |
| ttttcaaaat cggcattggc ccttccagtt ctcataccgt tggaccaatg aaagcgggta | 420 |
| aacaatttac cgacgatctg attgcccgta acctgcttaa agacgtgacc cgcgtggtgg | 480 |
| ttgacgtgta cggctcgctc tctctgaccg gtaaaggcca ccacactgat atcgccatta | 540 |
| ttatgggcct ggcgggtaac ctgccggata ccgtggatat cgattccatc cccagttta | 600 |
| tcaggatgt gaatactcat ggtcgcctga tgctggcaaa cggtcagcat gaagtggagt | 660 |
| tcccggttga tcagtgcatg aacttccacg ccgacaacct ttctctgcat gaaaacggta | 720 |
| tgcgcattac cgcgctggcg ggcgataaag tcgtttacag ccagacttac tactctattg | 780 |
| gcggtggctt tatcgttgat gaagagcatt ttggccagca ggatagcgca ccggttgaag | 840 |
| ttccttatcc gtacagttca gcagccgatc tgcaaaaaca ttgtcaggaa accgggctgt | 900 |

```
cactctctgg cctgatgatg aaaaacgagc tggcgctgca cagcaaagaa gagctggaac    960
agcacctggc gaacgtctgg gaagtcatgc gcggcggtat tgagcgcggt atttccaccg   1020
aaggcgtgtt gcctggcaaa ctgcgcgttc cacgccgtgc tgcggcacta cgccggatgc   1080
tggtcagcca ggataaaacc accactgacc cgatggcggt tgttgactgg atcaacatgt   1140
ttgcactggc agtgaacgaa gagaacgctg ctggcggtcg cgtggtgact gcgccgacta   1200
acggtgcgtg cggattatcc ccggcagttc tggcgtacta cgacaagttt atccgcgaag   1260
tgaacgctaa ctcactggct cgttacctgc tggtagccag cgccattggt tctctttata   1320
agatgaacgc gtcgatttct ggtgctgaag tgggttgcca gggtgaagtt ggcgtggcgt   1380
gctcaatggc ggcggctggt ctggcagaac tattaggcgc aagcccggcg caggtgtgca   1440
tcgcggcgga aatcgccatg gagcacaacc tcggtctgac gtgtgacccg gtcgccggac   1500
aggtacaggt gccatgcatc gagcgtaacg ccattgcggc agtaaaagcg gtgaacgccg   1560
cacgtatggc gctgcgccgt accagcgagc gcgcgtctg cctcgataaa gttatcgaaa    1620
ccatgtacga aacaggtaaa gatatgaacg ccaagtaccg cgaaacctct cgcggcggcc   1680
tggcaatgaa gatcgttgcc tgcgattaat cgctctccaa aggcctcgtt ttgcgaggcc   1740
tcttcccgat ttctcatcca gccgtagcct gttccggcat cgaatgttac ccttatcgcc   1800
tgatctttaa gggggttatc gtggctgttc atttgcttat tgtcgatgca ctgaatctta   1860
ttcgtcgcat tcatgccgtt caggggtcgc cctgtgtcga aacctgccag catgcgctcg   1920
atcagctcat tatgcacagc cagccaaccc acgcggtcgc cgttttttgat gatgaaaacc   1980
gcagtagcgg ctggcgtcat cagcgtttac cagattacaa agcgggtcga ccgccaatgc   2040
cggaagagtt gcacgacgag atgcctgcat tacgcgccgc ctttgagcaa cgcggcgtcc   2100
cgtgctggtc aaccagcggc aacgaagccg atgacttagc cgccacgctg gcggtcaaag   2160
tgacacaggc cgggcatcag gcaacgattg tttcgacaga taaaggctac tgtcagttac   2220
tttcaccgac attacgtatt cgtgattact tccagaaacg ttggctggat gcgccattta   2280
tcgataaaga atttggcgtt caaccgcagc agttgcccga ttactgggga cttgcgggga   2340
tcagcagttc aaaggtaccg ggtgttgcgg gaatcggacc aaaaagcgcc acgcagctgc   2400
tggtcgagtt tcagagtctg gagggatat atgagaatct ggatgcggtt gccgaaaagt   2460
ggcgcaaaaa attagaaacc cataaagaga tggcgtttct gtgccgcgat attgcccgct   2520
tacaaaccga tttgcatatc gacggcaatt tacagcaatt gcggttggta cggtaacggc   2580
gagccggata cgccgcaaac gtcgtatccg gcattatcac atcagcgcat ttaccaggcg   2640
gtatggtaaa gctctacaat atcctcaagc gttgcttcac gcgggttgcc accggtacaa   2700
acatcatcca gtgccgcctg cgccagtgcc ggaatgtctt ccttgcgtac accaacatca   2760
cgcaaatgtg gcggaatacc gacatcacgg ttgagagcaa acaccgcttc aacagcggca   2820
ttacgcgcct cttccaggct catacctcc actttcacgc ccataacgcg cgcgatatcg   2880
cggtacttct caccggtaaa gtcagcgtta taacgcatga catgcggtaa caggatggcg   2940
ttcgcaacac cgtgtggagt gttataaaac gcgcccagtg gatgcgccat accatgcacc   3000
aaccctaacc caacattcga gaagcccata cccgcaacat actgcccgag cgccattcct   3060
tctccggcat ccttatcacc agcaaccgat cctcgcagcg ccccagcaat gatttcaatc   3120
gctttaatgt gcagtgcatc ggttagcgcc cacgcgccac gggtaatata cccctcaata   3180
gcatgagtga gcgcatcgac acccgtcgca gctttcagcg ctggaggcat accatccatc   3240
```

```
atgtcagcgt caataaacgc cacctgcggg atatcatgcg gatcaacgca aacaaacttg    3300
cgccgtttct cttcgtcagt gatcacgtag ttaatggtca cttctgccgc agtacctgct    3360
gtggtaggaa ttgccagaat cggtacactg ggtttattgg tcggggaaag cccttccagg    3420
ctacgcacat cggcaaactc cgggttgttg ctgataatgc caatcgcttt acaagtatcc    3480
tgtggagaac caccaccaat agcgatcagg taatccgcgc cgctattctg gaatacaccg    3540
agcccttctt tgacgacagt aattgttggg ttgggcacta cgccgtcgta aatcgcccat    3600
gccagccctg cagcatccat cttatcggtc actttcgcca ccacgccgca ttgcaccagc    3660
gttttatcgg tgacgatcag cgccttctga taaccacggc gtttcacctc atcggttaaa    3720
gccccaacag caccccgacc aaaccatgcc gtttcgttca gaatcattct gttagccatc    3780
atccttctcc ttgttgcttt acgaaattac tcttcaattc gtaacccata ggttttgaat    3840
ttctccagca ctacggcaat ctcttcatcg ctcagcactg gcaccgggtc cgtaatcgcc    3900
agggtcgtca ggtaaagttg cgccagcact tcaacttcat gcgccagcca taacgctttt    3960
tccagattca cctcacaagc gataagccca tgatgttgta acaaagttgc cttacgattt    4020
ttgagagcca gcgcaacatg ttcagaaagt tcgcgtgttc caaggtcgc ataaggcgcg    4080 caaggaatag aattaccgcc agccgccgca atcatgtagt gaatagcggg gatcgatcgg    4140
ttaagaatgg aaactgccgt gcaatgaacg gcatgattgt gaacaaccgc gttggcatcc    4200
ggtctgcttt gataggctgc catatggaaa cgccattcgc ttgaggggag cttcttcc    4260 tcatgtttac cgttgccatc aataaagaca atatgcgact ccgtcagttt ttcatatgga    4320
atgcctgtag gcgtaatcag catcccatcc tgataacgta cactgacgtt ccccgctgtc    4380
ccctggttca gtcccaggcg ggtcatttcc aggcaagtgt caataatctg acgagcaagt    4440
ttatttcgtt ccattagcta cctctctctg attcaaaaca gggcaataat gttgttcctt    4500
tcacactatt gaattagccg tttaattacc caccatcttc ttcctgatta acaagaaaga    4560
aattcacaag cttatatttt gtgacctggt tcaactaatc acagtaaata actgcaagtt    4620
ctctttttat aaccccatta aaaatgaccg ctcttaaaaa tatttatcaa acggtcatt    4680 tttctattcc tccaagcccg gaatgaccgt tttcggcaca acaattaat acggtcatct    4740 gatttgtgtt ttttatgatt tattttctga acgggcatg aaatttcgat tattaaagtg    4800
atggtagtca cataaagtca ccttctagct aataagtgtg accgccgtca tattacagag    4860
cgttttttat ttgaaaatga atccatgagt tcatttcaga caggcaaata ttcactgata    4920
tgaagcccga actcgctggt tttgcacttt tgaaaacata accgattacg tgcttaagct    4980
tctgaaccta agaggatgct atgggaaaca catcaataca aacgcagagt taccgtgcgg    5040
tagataaaga tgcagggcaa agcagaagtt acattattcc attcgcgctg ctgtgctcac    5100
tgttttttct ttgggcggta gccaataacc ttaacgacat tttattatca aggcgcactc    5160 ccgtctgga taatgttttt tgcgccgaca tcataacggt tctggcaaat attctgaaat    5220
gagctgttga caattaatca tcggctcgta taatgtgtgg aattgtgagc ggataacaat    5280
ttcacacagg aaacagaatt cccctctaga ataatttg tttaacttta agaaggagat    5340
atacatatgg aacgtattgt tgttaccctg ggtgaacgta gctatccgat taccattgca    5400
agcggtctgt ttaatgaacc ggcaagcttt ctgccgctga aaagcggtga acaggttatg    5460
ctggttacca atgaaaccct ggcaccgctg tatctggata agttcgtgg tgttctggaa    5520 caggcaggcg ttaatgttga tagcgttatt ctgccggatg cgaacagta taaaagcctg    5580 gcagttctgg ataccgtttt taccgcactg ctgcagaaac cgcatggtcg tgataccacc    5640
```

```
ctggttgcac tgggtggtgg tgttgttggt gatctgaccg ttttgcagc cgcaagctat    5700 cagcgtggtg tgcgttttat tcaggttccg accaccctgc tgagccaggt tgatagcagc    5760
gttggtggta aaaccgcagt taatcatccg ctgggcaaaa atatgattgg tgcatttat     5820 cagcctgcca gcgttgttgt ggatctggat tgtctgaaaa ccctgcctcc gcgtgaactg    5880
gccagcggtc tggccgaagt tatcaaatat ggtattattc tggatggtgc cttcttcaat    5940
tggctggaag aaaatctgga tgccctgctg cgcctggatg gtccggcaat ggcatattgt    6000
attcgtcgtt gttgcgaact gaaagccgaa gttgttgcag cagatgaacg tgaaaccggt    6060
ctgcgtgcac tgctgaatct gggtcatacc tttggtcatg caattgaagc agaaatgggt    6120
tatggtaatt ggctgcatgg tgaagcagtt gcagccggta tggttatggc agcacgtacc    6180
agcgaacgtc tgggtcagtt tagcagcgca gaaacccagc gtattatcac gctgctgaaa    6240
cgtgcaggtc tgccggttaa tggtcctcgt gaaatgagcg cacaggcata tctgccgcac    6300
atgctgcgtg ataaaaaagt tctggcaggc gaaatgcgtc tgatcctgcc gctggcaatt    6360
ggtaaaagcg aagttcgtag cggtgttagc catgaactgg ttctgaatgc aattgccgat    6420
tgtcagagcg cataagaagg aggatctcat atgaactatc agaacgatga cctgcgcatc    6480
aaagaaatta agaactgct gcctccggtt gcactgctgg aaaaatttcc ggcaaccgaa    6540
aatgcagcaa ataccgttgc acatgcacgt aaagccattc acaaaattct gaaaggtaat    6600
gatgatcgcc tgctggttgt tattggtccg tgtagcattc atgatccggt tgccgcaaaa    6660
gaatatgcaa cccgtctgct ggcactgcgt gaagaactga agatgaact ggaaattgtg    6720 atgcgcgtgt attttgaaaa accgcgtacc accgttggtt ggaaaggtct gattaatgat    6780
ccgcacatgg ataacagctt tcagattaac gatggtctgc gtattgcccg taaactgctg    6840
ctggatatta atgatagcgg tctgcctgca gccggtgaat ttctgaatat gattacaccg    6900
cagtatctgg ccgatctgat gagctggggt gcaattggtg cacgcaccac cgaaagccag    6960
gttcatcgtg aactggcaag cggtctgagc tgtccggttg ctttaaaaa cggcaccgat    7020 ggcaccatta aagttgcaat tgatgcaatt aatgcagcgg gtgcaccgca ttgttttctg    7080
agcgttacca aatgggtca tagcgcaatt gttaatacca gcggtaatgg tgattgccat    7140
attattctgc gtggtggtaa agaaccgaat tattcagcaa acatgtggc cgaagttaaa    7200 gaaggtctga taaagcagg tctgccagca caggttatga ttgattttag ccatgcaaat    7260
agcagcaaac agttcaaaaa acaaatggat gttgtgccg atgtgtgtca gcagattgcc    7320
ggtggtgaaa aagcaattat tggtgttatg gttgaaagcc atctggtgga aggtaatcag    7380
agcctggaaa gcggtgaacc gctggcctat ggtaaaagca ttaccgatgc atgtattggt    7440
tgggaagata ccgatgccct gctgcgtcag ctggcaaatg cagttaaagc acgtcgtggt    7500
taagaaggag gatcctctag agtcgacctg caggcatgca agcttaacgg ctgacatggg    7560
aattagccat ggtccatatg aatatcctcc ttagttccta ttccgaagtt cctattctct    7620
agaaagtata ggaacttcgg cgcgcctacc tgtgacggaa gatcacttcg cagaataaat    7680
aaatcctggt gtccctgttg ataccgggaa gccctgggcc aacttttggc gaaaatgaga    7740
cgttgatcgg cacgtaagag gttccaactt tcaccataat gaaataagat cactaccggg    7800 cgtattttt gagttgtcga gattttcagg agctaaggaa gctaaaatgg agaaaaaaat    7860
cactggatat accaccgttg atatatccca atggcatcgt aaagaacatt ttgaggcatt    7920
tcagtcagtt gctcaatgta cctataacca gaccgttcag ctggatatta cggcctttt    7980
```

```
aaagaccgta agaaaaata agcacaagtt ttatccggcc tttattcaca ttcttgcccg    8040
cctgatgaat gctcatccgg aattacgtat ggcaatgaaa gacggtgagc tggtgatatg    8100
ggatagtgtt caccottgtt acaccgtttt ccatgagcaa actgaaacgt tttcatcgct    8160
ctggagtgaa taccacgacg atttccggca gtttctacac atatattcgc aagatgtggc    8220
gtgttacggt gaaaacctgg cctatttccc taaagggttt attgagaata tgttttttcgt   8280 ctcagccaat ccctgggtga gtttcaccag ttttgattta acgtggcca atatggacaa    8340 cttcttcgcc cccgttttca ccatgggcaa atattatacg caaggcgaca aggtgctgat    8400
gccgctggcg attcaggttc atcatgccgt tgtgatggc ttccatgtcg gcagatgctt    8460
aatgaataca acagtactgc gatgagtggc agggcgggc gtaaggcgcg ccatttaaat    8520
gaagttccta ttccgaagtt cctattctct agaaagtata ggaacttcga agcagctcca    8580
gcctacacaa tcgctcaaga cgtgtaatgc tgcaatctgc atgcaagctt ctgttttggc    8640
ggatgagaga agattttcag cctgatacag attaaatcag aacgcagaag cggtctgata    8700
aaacagaatt tgcctggcgg cagtagcgcg gtggtcccac ctgaccccat gccgaactca    8760
gaagtgaaac gccgtagcgc cgatggtagt gtggggtctc cccatgcgag agtagggaac    8820
tgccaggcat caaataaaac gaaaggctca gtcgaaagac tgggcctttc gttttatctg    8880
ttgtttgtcg gtgaacgctc tcctgagtag acaaatccg ccgggagcgg atttgaacgt    8940
tgcgaagcaa cggcccggag ggtggcgggc aggacgcccg ccataaactg ccaggcatca    9000
aattaagcag aaggccatcc tgacggatgg cctttttgcg tttctacaaa ctcttttgtt    9060
tattttctta aatacattca aatatgtatc cgctcatgag acaataaccc tgggggttct    9120
gaccatcggc cacgttggcg cagactttat cactctcgcc tccatgctgc gtatcccggt    9180 atgtatcac aacgttgaag agaccaaagt gtatcgtcct tctgcctggg ctgcgcacgg    9240
catggatatt gaaggccagg attaccgcgc ttgccagaac tacggtccgt tgtacaagcg    9300
ttaatacatt actccctgat gtgatgcccg gtcgctccgg ctaccgggcc tgaacaagca    9360
agagtggtta gccggataag caatgttatc cggctatatt gcaggagcga ttatgaaaca    9420
agaagttatc ctggtactcg actgtggcgc gaccaatgtc agggccatcg cggttaatcg    9480
gcagggcaaa attgttgccc gcgcctcaac gcctaatgcc agcgatatcg cgatggaaaa    9540
caacacctgg caccagtggt ctttagacgc cattttgcaa cgctttgctg attgctgtcg    9600
gcaaatcaat agtgaactga ctgaatgcca catccgcggt atcgccgtca ccacctttgg    9660
tgtggatggc gctctggtag ataagcaagg caatctgctc tatccgatta ttagctggaa    9720
atgtccgcga acagcagcgg ttatggacaa tattgaacgg ttaatctccg cacagcggtt    9780
gcaggctatt tctggcgtcg gagcctttag ttttcaatacg ttatataagt tggtgtggtt   9840
gaaagaaaat catccacaac tgctggaacg cgcgcacgcc tggctcttta tttcgtcgct    9900
gattaaccac cgtttaaccg gcgaattcac tactgatatc acgatggccg gaaccagcca    9960
gatgctggat atccagcaac gcgatttcag tccgcaaatt ttacaagcca ccggtattcc   10020
acgccgactc ttccctcgtc tggtggaagc gggtgaacag attggtacgc tacagaacag   10080
cgccgcagca atgctcggct taccgttgg cataccggtg atttccgcag gtcacgatac   10140
ccagttcgcc cttttttggcg ctggtgctga acaaaatgaa cccgtgctct cttccggtac   10200
atgggaaatt ttaatggttc gcagcgccca ggttgatact tcgctgttaa gtcagtacgc   10260
cggttccacc tgcgaactgg ataaccaggc agggttgtat aacccaggta tgcaatggct   10320
ggcatccggc gtgctggaat gggtgagaaa actgttctgg acggctgaaa caccctggca   10380
```

```
aatgttgatt gaagaagctc gtctgatcgc gcctggcgcg gatggcgtaa aaatgcagtg    10440
tgatttattg tcgtgtcaga acgctggctg gcaaggagtg acgcttaata ccacgcgggg    10500
gcatttctat cgcgcggcgc tggaagggtt aactgcgcaa ttacagcgca atctacagat    10560
gctggaaaaa atcgggcact ttaaggcctc tgaattattg ttagtcggtg gaggaagtcg    10620
caacacattg tggaatcaga ttaaagccaa tatgcttgat attccggtaa aagttctcga    10680
cgacgccgaa acgaccgtcg caggagctgc gctgttcggt tggtatggcg tagggggaatt    10740 taacagcccg gaagaagccc gcgcacagat tcattatcag taccgttatt tctacccgca    10800
aactgaacct gaatttatag aggaagtgtg aaatgctgaa acaatttcg ccgttaattt    10860 ctcccgaact attgaaagtg ctggcagaga tgggacatgg agatgaaatt atttttccg    10920 atgctcactt tcccgcccat tcgatgggac cgcaggtgat ccgcgctgat ggcctgttgg    10980
tgagcgactt gctccaggcg attatcccgt tatttgaact ggacagttat gcaccgccgc    11040
tggtgatgat ggcggcggta gaaggtgaca ctctcgatcc tgaagtagaa cgacgttacc    11100
gtaatgcgct ttcactacaa gccccgtgtc ctgacatcat ccgcatcaat cgttttgcgt    11160
tttatgaacg ggcgcaaaaa gccttttgcga tcgttatcac aggcgaacga gcgaagtacg    11220
ggaatattct tttaaaaaaa ggggtaacac cgtaatctca taccggtacg cccgcatgac    11280
gcgggcggtt atcgaatgat ggggtgaaaa atatgaaagc ggcacgccag caagcgatag    11340
tcgacctgct gctgaaccat accagcctga ccacggaagc tctctctgaa cagctaaagg    11400
tcagtaaaga aaccattcgt cgcgatctca atgaattaca dacgcagggt aaaattctgc    11460
gcaatcatgg acgcgctaaa tatatccacc gtcaaaatca agacagtggc gatcccttc    11520 acatcaggct gaaaagccat tatgcgcata aagcagatat cgcgcgcgag gcgctcgcgt    11580
ggattgaaga agggatggtg atagccttag acgccagttc aacttgctgg tatctggcac    11640
gccagttgcc tgacatcaac attcaggtct tcaccaatag ccatccgatt tgccatgaac    11700
tcggtaaacg cgaacgcatt caactgatca gttccggcgg cacacttgag cgcaaatatg    11760
gctgttacgt caatccctcg ctgatttccc aacttaaatc gctggaaatc gatctgttta    11820
ttttttcttg tgaagggatc gatagcagcg gcgcactgtg ggactccaat gcgatcaacg    11880
ctgattacaa atcgatgcta ttaaaacgtg ccgcgcaatc gttgttattg attgataaaa    11940
gtaaatttaa tcgttcaggg gaagcccgca tcgggcatct ggatgaggta acgcacatta    12000
tttctgatga gcgccaggtt gcaacttctt tggtaacagc ctgacggaaa gggtagcagg    12060
ccggagacga cgccccggcc ttgcctgtta tcgctcgtcg cgacgaccac ccaccgcagc    12120
ccagatgcgg cggacgtgca ccgtcacttc ttcgcgatcg tgatacaact gccgcgcctg    12180
aatctgagca tttatgccat gttcatcaag ctgtgcctga atatacgcca gattgtgtga    12240
cacttcttcg tagcgttttt tcatcggcag tttgaggttg aaaatggttt cacggcacca    12300
gccattaacc agccactgcg ccatcaatgc cgcaactttc gccggttttt caaccatatc    12360
gcataccatc caggagatat tgctgcgcgt cggacggaat ttgaaaccgt cttccgcag    12420 ccacgtcacc tgtccggtat ccatcagact ttgcgccatc gggccgttgt cgacggaata    12480
aacccacatg ttgcgc                                                    12496
```

<210> SEQ ID NO 17
<211> LENGTH: 28
<212> TYPE: DNA
<213> ORGANISM: Artificial Sequence
<220> FEATURE:

```
<223> OTHER INFORMATION: Artificial Sequence

<400> SEQUENCE: 17
ggcctatttc cctaaagggt ttattgag                                    28

<210> SEQ ID NO 18
<211> LENGTH: 29
<212> TYPE: DNA
<213> ORGANISM: Artificial Sequence
<220> FEATURE:
<223> OTHER INFORMATION: Artificial Sequence

<400> SEQUENCE: 18
gacgatacac tttggtctct tcaacgttg                                   29
```

METHOD FOR PRODUCING PHENOL FROM RENEWABLE RESOURCES BY FERMENTATION

This application is a 371 of International Patent Application No. PCT/EP2013/073688, filed Nov. 13, 2013, which claims foreign priority benefit under 35 U.S.C. §119 of European Patent Application No. 12192342.9, filed Nov. 13, 2012, the disclosures of which patent applications are incorporated herein by reference.

TECHNICAL FIELD

The invention relates to the field of producing phenol from renewable sources, such as e.g. biomass in a suitable recombinant host.

INTRODUCTION

Phenol is currently produced at several million tonnes per year from fossil raw materials, predominantly by the cumene process, i.e. a chemical process. Such fossil raw materials are not renewable as opposed to raw materials which are renewable, such as the renewable resource "biomass". A production process based on renewable resources, such as biomass, would achieve independence from fossil resources and would have the potential of saving large amounts of $CO_2$ emissions.

Phenol is a chemical intermediate used in industry in the production of phenolic resins, bisphenol A caprolactame and other chemicals. Phenol that is based on renewable resources, which is referred to here in the context of the invention as "biophenol", is strongly desired in order to reduce production cost and become independent of fossil resources. More importantly, chemical companies have committed themselves to reduce $CO_2$ emissions both for their own processes as well as by increasing the use of renewable resources in their raw materials. Biophenol has a high potential of avoiding fossil resources and saving $CO_2$ emissions, accordingly.

The production of chorismate in bacteria was described in Sprenger G A, "From scratch to value: engineering *Escherichia coli* wild type cells to the production of L-phenylalanine and other fine chemicals derived from chorismate", *Appl Microbiol Biotechnol* 2007, 75:739-749.

The production of phenol in bacteria has been described by Wierckx N J P et al., "Engineering of solvent-tolerant *Pseudomonas putida* S12 for bioproduction of phenol from glucose", *Appl Environ. Microbiol.* 2005. 71:8221-8227.

However, the biosynthesis pathway used by Wierckx et. al first builds up the molecule tyrosine from chorismate by incorporating an amino group from glutamate, and then breaks it down to phenol releasing the amino group again. This pathway comprises more reaction steps, and is energetically less favouorable than the method according to the invention due to the longer pathway which leads to the deamination of glutamate. Using tyrosine as an intermediate for the biosynthesis of phenol is also a disadvantage because tyrosine is a strong inhibitor of the activity of the genes in the aromatic amino acid pathway. The inhibition takes place at genome level (gene repression), transcriptome level and metabolome level (feedback inhibition). In contrast, the method according to the invention converts chorismate directly to phenol, as described below, which is less complex, energetically more efficient and has a higher potential of yielding high production rates of phenol.

In addition to the above pathway over tyrosine to produce phenol in bacteria, it is also known that phenol can be produced by chemical conversion of shikimic acid, wherein the shikimic acid is produced by fermentation (Gibson J M et al., Benzene-Free Synthesis of Phenol, *Angew. Chem.* 2001 113(10):1999-2002).

The biosynthesis of 4-hydroxybenzoate over tyrosine was also reported. Meinen et al. used the biosynthesis pathway over tyrosine (Meijnen J P et al., Improved p-hydroxybenzoate production by engineered *Pseudomonas putida* S12 by using a mixed-substrate feeding strategy. *Appl Microbiol Biotechnol.* 2011. 90(3):885-93.).

WO2012063862 describes a method for producing phenol by fermentation. The pathway over chorismate and 4-hydroxybenzoate was used by introducing the genes for a chorismate-pyruvate lyase and a 4-hydroxybenzoate decarboxylase in a *Corynebacterium glutamicum* strain. However, phenol is toxic for *Corynebacterium glutamicum* and this strain stops to grow at low concentrations of phenol. The growth phase and the production phase are therefore separated in a two-step process, wherein the second step is performed in a different medium than the first and the redox potential is lowered to −450 mV. Combined growth and production using only one fermentation vessel is not possible according to the invention reported in WO2012063862. For the same reason it is not possible to run a continuous fermentation with in-situ product removal where the biomass is regenerating itself by growth.

DEFINITIONS

The term "host" within the meaning of the invention can comprise any host that is capable of producing chorismate, either naturally, only after transformation, or in addition to the naturally present chorismate following transformation. A "host" according to the invention can be selected from the group consisting of bacteria, yeast and fungi.

The term "genetic modification" within the meaning of the invention can comprise deletions as well as transformations. For example, a genetic modification can be a deletion or a transformation that causes the host to overproduce chorismate. Such overproduction of chorismate in the host can be achieved by introducing one or more genetic modifications in the host. Accordingly, the host can comprise one or more genetic modifications to overproduce chorismate. These genetic modifications can have the effect that the host is producing chorismate at levels that are elevated, above the normal, endogenous physiological levels that are present in the host by nature.

The term "transformation" within the meaning of the invention comprises plasmid transformation as well as chromosomal transformation. In plasmid transformation the transformed DNA is uncut and circular and therefore is held extrachromosomally in the host. In chromosomal transformation the transformed DNA is cut and therefore linear and can thus be integrated into the chromosomal genome of the host to be transformed. Essentially, for chromosomal transformation, the host can be transformed with a short piece of linear DNA that can be integrated into the chromosomal genome of the host to be transformed.

The term "in-situ product recovery" within the meaning of the invention refers to the removal of phenol directly from the fermentation broth by using a suitable technique, while the fermenter broth is continued to be used in the fermentation. This may include circulating the fermentation broth through an external apparatus where the phenol is removed from the fermentation broth before the fermentation broth is partly recycled to the fermenter. The cells may or may not be retained in the fermenter in this case. Another option is to remove the phenol from the fermentation broth while the fermenter broth remains in the fermenter.

DESCRIPTION

The invention relates to a method for whole cell biosynthesis of phenol from biomass as the starting material. Typically a source containing a significant proportion of fermentable sugars can be used in the method according to the invention. These sugars can include polysaccharides such as di-saccharides, e.g. saccharose, or tri-saccharides, e.g. kestose, as well as C-6 monosaccharides such as glucose, fructose or mannose and C-5 monosaccharides such as xylose and arabinose. A microbial strain, preferably a bacterial strain or a yeast strain, that is capable of converting sugar to phenol would enable the production of phenol from a wide range of renewable resources including sugar beet and sugar cane, starch-containing plants such as corn, wheat and rye, as well as lignocellulose e.g. from straw, wood or bagasse.

Given the major disadvantages of the above methods known in the art that usually are less efficient in energetic terms and also more complex with regard to the synthesis of phenol, there has been a need in the art for an improved method for producing phenol. It has therefore been the problem of the invention to provide a method for producing phenol from renewable sources that avoids the disadvantages of methods known in the art that are less efficient in energetic terms and more complex with regard to the synthesis of phenol.

The invention has solved said problem by providing a method of generating a recombinant host strain for producing phenol as described herein. The invention has further solved said problem by providing a recombinant host strain capable of producing phenol as described herein. The invention has further solved said problem by providing a method of producing phenol in the recombinant host strain. The invention has further solved said problem by providing a method and associated recombinant strain comprising an oxygen-tolerant hydroxybenzoate decarboxylase that is not sensitive to oxygen and is fully active at normal redox conditions, thus allowing phenol production at aerobic conditions. The invention has further solved said problem by providing a host strain that is resistant to phenol, thus allowing combined growth and phenol production at phenol concentrations high enough to enable production by continuous fermentation with the option of in-situ product recovery.

In particular, the invention has solved said problem by providing a method of generating a recombinant host strain for producing phenol, comprising the steps of:
a) providing a host comprising chorismate (CHO),
b) transforming said host with a first nucleic acid sequence comprising ubiC (SEQ ID NO: 1) encoding chorismate lyase, and
c) transforming said first transformant with a second nucleic acid sequence encoding an oxygen-tolerant 4-hydroxybenzoate decarboxylase, thereby generating a recombinant host that is capable of producing phenol under aerobic conditions,
wherein step b) and step c) are carried out simultaneously or sequentially.

Step a) of the method can make use of chorismate (CHO) that is present in the host. Chorismate is a key intermediate in the implemented pathway (see FIG. 1 and FIG. 2). It is a shared precursor for all three aromatic amino acids and is therefore naturally present in all organisms capable of producing aromatic amino acids, which includes all common microorganisms. Intracellular chorismate can therefore be produced from all fermentable sugars.

Step b) of the method provides the host with a first nucleic acid sequence, preferably a gene, the product of which converts chorismate (CHO) to 4-hydroxybenzoate (4-HB). ubiC (SEQ ID NO: 1) encodes the enzyme chorismate lyase that converts chorismate to 4-hydroxybenzoate (4-HB), thereby generating a recombinant host that overexpresses chorismate lyase (see FIG. 2 and FIG. 3). Thus, in a preferred embodiment of the invention, the first nucleic acid sequence is SEQ ID NO: 1.

Step c) of the method according to the invention additionally provides the host with a second nucleic acid sequence, preferably a gene cluster, the product of which converts 4-hydroxybenzoate (4-HB) to phenol, by introducing a nucleic acid into the host encoding an oxygen-tolerant 4-hydroxybenzoate decarboxylase (see e.g. FIG. 2 and FIG. 3). Said nucleic acid in step b) can comprise the gene cluster hbdBCD (SEQ ID NO 2) that expresses 4-hydroxybenzoate decarboxylase. The gene cluster hbdBCD of step c) can be derived from the *E. coli* strain *E. coli* O111:B4.

Thus, in a further embodiment of the method according to the invention, said second nucleic acid sequence comprises the gene cluster hbdBCD, as defined in SEQ ID NO 2. The enzyme encoded by SEQ ID NO: 2 is a 4-hydroxybenzoate decarboxylase that is oxygen-tolerant. Thus, in a preferred embodiment of the invention, said second nucleic acid sequence is SEQ ID NO: 2.

Thus, the invention has solved the above problem by providing a method of generating a recombinant host strain for producing phenol, comprising the steps of:
a) providing a host comprising chorismate (CHO),
b) transforming said host with a first nucleic acid sequence comprising ubiC (SEQ ID NO: 1) encoding chorismate lyase that converts chorismate (CHO) to 4-hydroxybenzoate (4-HB), and
c) transforming said first transformant with a second nucleic acid sequence encoding an oxygen-tolerant 4-hydroxybenzoate decarboxylase that converts 4-hydroxybenzoate (4-HB) to phenol, thereby generating a recombinant host that is capable of producing phenol under aerobic conditions,
wherein step b) and step c) are carried out simultaneously or sequentially.

In a preferred embodiment of the invention, said first nucleic acid sequence is SEQ ID NO: 1. In a further embodiment of the method according to the invention, said second nucleic acid sequence comprises the gene cluster hbdBCD, as defined in SEQ ID NO 2. The enzyme encoded by SEQ ID NO: 2 is a 4-hydroxybenzoate decarboxylase that is oxygen-tolerant. This, in a preferred embodiment of the invention, said second nucleic acid sequence is SEQ ID NO: 2.

Thus, the minimum requirements for producing phenol in a recombinant host according to the invention are the presence of chorismate in the host and the first nucleic acid sequence comprising ubiC (SEQ ID NO: 1) and the second nucleic acid sequence encoding an oxygen-tolerant 4-hydroxybenzoate decarboxylase that preferably is hbdBCD, as defined in SEQ ID NO: 2. The chorismate present in the host can be the endogenous chorismate that is produced naturally by the host, or it can be chorismate that is overproduced by the host, if said host comprises one or more genetic modifications to overproduce chorismate.

The first and second nucleic acid sequences transformed into the host in steps b) and c) can be on the same plasmid, on different plasmids or on the chromosome (chromosomal integration, e.g. Example 5). If the first and second nucleic acid sequences transformed into the host are on the same plasmid then step b) and step c) of the method can be carried out simultaneously (e.g. see Example 1). If the first and second nucleic acid sequences transformed into the host are on different plasmids then step b) and step c) of the method can be carried out sequentially. For example, the gene ubiC (SEQ ID NO: 1) can be transformed on a first plasmid into the host, and the gene cluster hbdBCD (SEQ ID NO: 2) can be transformed on a second plasmid into the host (see e.g. Example 3). In one embodiment, the host strain is transformed with ubiC and hbdBCD that are present on the same plasmid (e.g. see Example 1, pJF119ubiChbdBCD). In another embodiment, the host strain is transformed with ubiC (SEQ ID NO: 1) on the first plasmid pJF119 and with hbdBCD (SEQ ID NO: 2) on the second plasmid pACYC (e.g. see Example 3).

The technical advantage of the method of the invention over the prior art methods described above is that the economic feasibility of phenol production in a large scale production facility is improved. The invention allows a one-step conversion of sugar into phenol in a single vessel using continuous fermentation with in-situ product removal at aerobic conditions. This improves the sugar yield and the space time yield significantly. Compared to a fed-batch fermentation a continuous fermentation has a much better overall sugar yield since less sugar is needed to generate biomass which in case of a fed-batch fermentation needs to be generated for every new batch. The overall space-time yield is improved since no time is lost between the production phases as would be the case in a fed-batch fermentation (e.g. for harvesting the product, cleaning and sterilizing the fermenter, generating the biomass). Furthermore, the one-step conversion allows production using only one fermentation vessel. That reduces the complexity of the process and the capital expenditure for the production facility.

Compared to the synthesis pathway over tyrosine reported by Wierckx et al., the implemented synthesis pathway is less complex, more energy efficient and avoids large intracellular concentrations of tyrosine which would inhibit the biosynthesis pathway to phenol. As a result the method according to the invention is much more efficient, since it is able to achieve a better sugar yield (due to the energy efficiency) and a better space-time-yield (due to the shorter pathway and the avoidance of tyrosine as an intermediate), as compared to the methods known in the art.

In a further embodiment of the method according to the invention the host of step a) can overproduce chorismate (CHO). Such overproduction of chorismate in the host can be achieved by introducing one or more genetic modifications in the host. Accordingly, in a further embodiment of the method of the invention, the host can comprise one or more genetic modifications to overproduce chorismate. These genetic modifications have the effect that the host is producing chorismate at levels that are elevated, above the normal, endogenous physiological levels. Since more substrate is provided for the subsequent reactions in step b) (chorismate, CHO, to 4-hydroxybenzoate, 4-HB, by the ubiC gene product) and in step c) (4-HB to phenol by the hbdBCD gene product), more end product, i.e. phenol, is produced.

Such one or more genetic modifications can comprise a deletion of one or more of tyrR, pheA and tyrA that can be introduced into the host.

The TyrR protein, encoded by the gene tyrR, represses the expression of several of the genes in the common part of the aromatic amino acid pathway by binding to recognition sequences referred to as TyrR boxes. The TyrR protein is modulated by the presence of aromatic amino acids. In particular, the presence of tyrosine and ATP allows it to self-associate into a hexamer which can also bind to weak TyrR boxes some of which overlap the promotors of the genes in the aromatic amino acid pathway. In some cases the mechanism of repression involves exclusion of the RNA polymerase from the promotors, while in others it interferes with the ability of bound RNA polymerase to form open complexes or to exit the promotors. By deleting tyrR the regulatory effects caused by TyrR can be avoided completely, as shown in FIG. 2. The deletion of tyrR can be achieved by using the λ red recombinase according to the protocol by Datsenko and Wanner, as described in Example 1. Here, tyrR can be deleted by using the tyrR::FRT-kan cassette that is shown in SEQ ID NO:3, and as described in Example 1.

The gene pheA encodes for a bifunctional enzyme which catalyses the conversion of chorismate to prephenate (chorismate mutase) as well as the conversion of prephenate to keto-phenylpyruvate. The gene tyrA also encodes for a bifunctional enzyme which also catalyses the conversion of chorismate to prephenate (chorismate mutase) as well as the conversion of prephenate to 4-hydroxyphenylpyruvate (prephenate dehydrogenase). By deleting both the pheA and the tyrA gene the pathway from chorismate to phenylalanine and tyrosine can be completely inactivated since all chorismate activity is removed as well as the prephenate dehydratase and the prephenate dehydrogenase activity, as shown in FIG. 2. Deletion of pheA and tyrA can be achieved by using the pheAtyrA::FRT-CAT cassette that is shown in SEQ ID NO:4, as also described in Example 1.

In further embodiments of the invention, one, two or all three of tyrR, pheA and tyrA can be deleted in the host strain used. In a preferred embodiment of the invention, all three of the genes tyrR, pheA and tyrA are deleted in the host (ΔtyrRpheAtyrA), so that chorismate is overproduced. One example of such a recombinant strain carrying all three deletions is E. coli BW25113 ΔtyrRpheAtyrA that is listed in Table 1. The generation of the strain E. coli BW25113 ΔtyrR ΔpheAtyrA is described in Example 1.

In a further embodiment of the method said one or more genetic modifications to overproduce chorismate can comprise a transformation with one or more of aroG (SEQ ID NO: 9), aroG$^{fbr}$ (SEQ ID NO: 10), aroB (SEQ ID NO: 11) and aroL (SEQ ID NO: 12). The host can be transformed individually with each one of aroG (SEQ ID NO: 9), aroG$^{fbr}$ (SEQ ID NO: 10), aroB (SEQ ID NO: 11) and aroL (SEQ ID NO: 12). The host can also be transformed with each combination of aroG (SEQ ID NO: 9), aroG$^{fbr}$ (SEQ ID NO: 10), aroB (SEQ ID NO: 11) and aroL (SEQ ID NO: 12) so that an optimal overproduction of chorismate is achieved.

The reactions catalysed by the gene products of aroG (SEQ ID NO: 9), aroG$^{fbr}$ (SEQ ID NO: 10), aroB (SEQ ID NO: 11) and aroL (SEQ ID NO: 12) are depicted in FIG. 2. They all result in an overproduction of chorismate in the host.

The gene product of aroG (SEQ ID NO: 9) catalyses the reaction from E4P to DAHP, as shown in FIG. 2.

aroG$^{fbr}$ (SEQ ID NO: 10) encodes for the same enzyme, except for a G to A mutation which makes the enzyme resistant to feedback inhibition, as reported by Kikuchi et al (Kikuchi, Y., Tsujimoto, K., Kurahashi, O. (1997) *Applied and Environmental Microbiology* 63 761-762) and shown in FIG. 6.

The gene product of aroB (SEQ ID NO: 11) catalyses the reaction from DAHP to 3DQ, as shown in FIG. 2.

The gene product of aroL (SEQ ID NO: 12) catalyses the reaction from SHI to SHI3P, as shown in FIG. 2.

The transformation of one or more of these genes results in an overproduction of chorismate in the host. Thus, in one embodiment of the method of the invention the host can comprise one or more genetic modifications to overproduce chorismate, wherein said one or more genetic modifications can be a transformation with one or more of aroG (SEQ ID NO: 9), aroG$^{fbr}$ (SEQ ID NO: 10), aroB (SEQ ID NO: 11) and aroL (SEQ ID NO: 12).

The transformation of the host with one or more of aroG (SEQ ID NO: 9), aroG$^{fbr}$ (SEQ ID NO: 10), aroB (SEQ ID NO: 11) and aroL (SEQ ID NO: 12) can be done as a single transformation step, wherein the genes that are transformed into the host are on the same plasmid. However, these transformations can also be performed in such a way that the genes that are introduced into the host are on separate plasmids or integrated directly on the chromosome.

In a further embodiment of the method said one or more genetic modifications that can be present in the host can comprise a deletion of one or more of tyrR, pheA and tyrA and can further comprise a transformation with one or more of aroG (SEQ ID NO: 9), aroG$^{fbr}$ (SEQ ID NO: 10), aroB (SEQ ID NO: 11) and aroL (SEQ ID NO: 12).

In a particularly preferred embodiment of the method, the host of step a) is subjected to deleting all three of the genes tyrR, pheA and tyrA thereby generating the host ΔtyrRpheAtyrA, preferably *E. coli* BW25113 ΔtyrRpheAtyrA that is listed in Table 1 and described in Example 1, so that chorismate is overproduced. The host ΔtyrRpheAtyrA can subsequently be transformed with ubiC (SEQ ID NO: 1) in step b) and with hbdBCD (SEQ ID NO: 2) in step c), simultaneously or sequentially, thereby generating a host ΔtyrRpheAtyrA transformed with ubiC and hbdBCD. One example of such a strain is *E. coli* BW25113 ΔtyrRpheAtyrA transformed with ubiC and hbdBCD, as listed in Table 1, and as further described in Example 1 (*E. coli* BW25113 ΔtyrR ΔpheAtyrA).

In a further particularly preferred embodiment of the method, the host of step a) can be subjected to deleting all three of the genes tyrR, pheA and tyrA, thereby generating the host ΔtyrRpheAtyrA, so that chorismate is overproduced, which is then transformed with aroL (SEQ ID NO:12) and with ubiC (SEQ ID NO: 1) in step b) and with hbdBCD (SEQ ID NO: 2) in step c) of the method according to the invention, thereby generating a host ΔtyrRpheAtyrA transformed with aroL, ubiC and hbdBCD. One example of such a strain is *E. coli* BW25113 ΔtyrRpheAtyrA transformed with aroL, ubiC and hbdBCD, as listed in Table 1, and as further described in Example 2.

In a particularly preferred embodiment, the genetic modification to overproduce chorismate comprises a transformation with aroG$^{fbr}$ (SEQ ID NO: 10), aroB (SEQ ID NO: 11), aroL (SEQ ID NO: 12), ubiC (SEQ ID NO: 1) and hbdBCD (SEQ ID NO: 2). Thus, one particularly preferred embodiment of the method according to the invention can generate the recombinant strain ΔtyrR ΔpheAtyrA transformed with aroG$^{fbr}$ (SEQ ID NO: 10), aroB (SEQ ID NO: 11), aroL (SEQ ID NO: 12) and ubiC (SEQ ID NO: 1) and hbdBCD (SEQ ID NO: 2).

In another particularly preferred embodiment, the genetic modification to overproduce chorismate comprises a transformation with aroG$^{fbr}$ (SEQ ID NO: 10), ubiC (SEQ ID NO: 1) and hbdBCD (SEQ ID NO: 2). Thus, one particularly preferred embodiment of the method according to the invention can generate the recombinant strain ΔtyrR ΔpheAtyrA transformed with aroG$^{fbr}$ (SEQ ID NO: 10) and ubiC (SEQ ID NO: 1) and hbdBCD (SEQ ID NO: 2).

In another particularly preferred embodiment, the genetic modification to overproduce chorismate comprises a transformation with aroG$^{fbr}$ (SEQ ID NO: 10), aroL (SEQ ID NO: 12), ubiC (SEQ ID NO: 1) and hbdBCD (SEQ ID NO: 2). Thus, one particularly preferred embodiment of the method according to the invention can generate the recombinant strain ΔtyrR ΔpheAtyrA transformed with aroG$^{fbr}$ (SEQ ID NO: 10), aroL (SEQ ID NO: 12) and ubiC (SEQ ID NO: 1) and hbdBCD (SEQ ID NO: 2).

The host that can be used for the method according to the invention can be selected from the group consisting of bacteria, yeast and fungi. In a preferred embodiment, the bacterium is an *Escherichia coli* strain. The *Escherichia coli* strain can be selected from the group consisting of *E. coli* BW25113, *E. coli* DH10b, and *E. coli* LJ110. In a particularly preferred embodiment of the method according to the invention, *E. coli* BW25113 ΔtyrRpheAtyrA is used, as listed in Table 1 and as described in Example 1.

In a further embodiment of the method according to the invention the host can be a phenol-resistant host, preferably a phenol-resistant bacterium, more preferably a phenol-resistant *Pseudomonas putida* strain, more preferably *Pseudomonas putida* S12 and most preferably *Pseudomonas putida* S12 ΔpheApobA.

The transformation steps b) and c) that are performed in the method according to the invention can comprise plasmid transformation or chromosomal transformation. In plasmid transformation the transformed DNA is uncut and circular and therefore is held extrachromosomally in the host. In chromosomal transformation the transformed DNA is cut and therefore linear and can thus be integrated into the chromosomal genome of the host to be transformed.

The invention further provides a recombinant host strain obtainable by the method according to the invention, as described above.

In one embodiment, the recombinant host strain comprises chorismate and further comprises a first nucleic acid sequence comprising ubiC (SEQ ID NO: 1) and a second nucleic acid sequence encoding an oxygen-tolerant 4-hydroxybenzoate decarboxylase, wherein the recombinant strain is capable of producing phenol under aerobic conditions.

In a further embodiment of the host strain according to the invention said second nucleic acid sequence comprises hbdBCD, as defined in SEQ ID NO: 2.

In a further embodiment, the recombinant host strain can overproduce chorismate. Such overproduction of chorismate in the host can be achieved by introducing one or more genetic modifications in the host. Accordingly, in a further embodiment, the host strain can comprise one or more genetic modifications to overproduce chorismate. These genetic modifications have the effect that the host is producing chorismate at a higher rate than normal. Since substrate is provided at a higher rate for the subsequent reactions in step b) (chorismate, CHO, to 4-hydroxybenzoate, 4HB, by the ubiC gene product) and in step c) (4-hydroxybenzoate, 4HB, to phenol by the hbdBCD gene product) the end product, i.e. phenol, is produced at a higher rate.

In one embodiment, the recombinant host strain comprises one or more genetic modifications, wherein said genetic modification comprises a deletion of one or more of tyrR, pheA and tyrA. These genes and their gene products, as well as their deletion, have been described above.

In further embodiments of the invention, one, two or all three of tyrR, pheA and tyrA can be deleted in the recombinant host strain of the invention. In a preferred embodiment of the invention, all three of the genes tyrR, pheA and tyrA are deleted in the host, so that chorismate is overproduced (ΔtyrRpheAtyrA). One example of such a recombinant strain carrying all three deletions is *E. coli* BW25113 ΔtyrRpheAtyrA that is listed in Table 1, and as described in Example 1.

In a further embodiment, the recombinant host strain comprises one or more genetic modifications, wherein said genetic modification comprises a transformation with a nucleic acid sequence comprising one or more of aroG (SEQ ID NO: 9), aroG$^{fbr}$ (SEQ ID NO: 10), aroB (SEQ ID NO: 11) and aroL (SEQ ID NO: 12). These genes and their gene products have been described above.

In a further embodiment, the recombinant host strain comprises one or more genetic modifications, wherein said genetic modification comprises a deletion of one or more of tyrR, pheA and tyrA; and further comprises a transformation with one or more of aroG (SEQ ID NO: 9), aroG$^{fbr}$ (SEQ ID NO: 10), aroB (SEQ ID NO: 11) and aroL (SEQ ID NO: 12). These genes and their gene products have been described above.

In a particularly preferred embodiment of the recombinant host strain of the invention, the genetic modification to overproduce chorismate comprises a transformation with aroG (SEQ ID NO: 10), aroB (SEQ ID NO: 11), aroL (SEQ ID NO: 12), ubiC (SEQ ID NO: 1) and hbdBCD (SEQ ID NO: 2). Thus, one particularly preferred embodiment of the recombinant host strain according to the invention is the recombinant strain ΔtyrR ΔpheAtyrA transformed with aroG$^{fbr}$ (SEQ ID NO: 10), aroB (SEQ ID NO: 11), aroL (SEQ ID NO: 12) and ubiC (SEQ ID NO: 1) and hbdBCD (SEQ ID NO: 2).

In another particularly preferred embodiment of the recombinant host strain of the invention, the genetic modification to overproduce chorismate comprises a transformation with aroG$^{fbr}$ (SEQ ID NO: 10), aroL (SEQ ID NO: 12), ubiC (SEQ ID NO: 1) and hbdBCD (SEQ ID NO: 2). Thus, one particularly preferred embodiment of the recombinant host strain according to the invention is the recombinant strain ΔtyrR ΔpheAtyrA transformed with aroG$^{fbr}$ (SEQ ID NO: 10), aroL (SEQ ID NO: 12) and ubiC (SEQ ID NO: 1) and hbdBCD (SEQ ID NO: 2).

In another particularly preferred embodiment of the recombinant host strain of the invention, the genetic modification to overproduce chorismate comprises a transformation with aroG$^{fbr}$ (SEQ ID NO: 10), ubiC (SEQ ID NO: 1) and hbdBCD (SEQ ID NO: 2). Thus, one particularly preferred embodiment of the method according to the invention can generate the recombinant strain ΔtyrR ΔpheAtyrA transformed with aroG$^{fbr}$ (SEQ ID NO: 10) and ubiC (SEQ ID NO: 1) and hbdBCD (SEQ ID NO: 2).

In a further embodiment, the recombinant host strain can be selected from the group consisting of bacteria, yeast and fungi. In a preferred embodiment, the bacterium is an *Escherichia coli* strain. In a further embodiment, said *Escherichia coli* strain can be selected from the group consisting of *E. coli* BW25113, *E. coli* DH10b, and *E. coli* LJ110. In a particularly preferred embodiment of the recombinant host strain according to the invention, *E. coli* BW25113 ΔtyrRpheAtyrA is used, as listed in Table 1, and as described in Example 1.

In a further embodiment of the recombinant strain according to the invention, said host can be a phenol-resistant host, preferably a phenol-resistant bacterium, more preferably a phenol-resistant *Pseudomonas putida* strain, more preferably *Pseudomonas putida* S12 and most preferably *Pseudomonas putida* S12 ΔpheApobA.

The deletion of pheA in *Pseudomonas putida*, as indicated by ΔpheA, inactivates the conversion of chorismate to prephenate (the chorismate mutase reaction, CHO to PREPH, see FIG. 2) thereby inactivating the pathway to phenylalanine and tyrosine. Unlike *E. coli*, *Pseudomonas putida* does not possess two isoenzymes for the chorismate mutase reaction, so it is sufficient to delete the pheA gene in *Pseudomonas putida* to inactivate the tyrosine and phenylalanine pathway. The gene pobA catalyses the conversion of 4-hydroxybenzoate to protocatechuate (4-hydroxybenzoate hydroxylase) which enables *Pseudomonas putida* to degrade 4-hydroxybenzoate. Deleting pheA and pobA, as indicated by ΔpheApobA, thus increases the availability of 4-hydroxybenzoate for phenol production, as the competing pathways are inactivated. *E. coli* does not have a hydroxybenzoate hydroxylase, so there is no corresponding deletion to be made if *E. coli* is used as the host.

The invention further provides a method of producing phenol in a recombinant host comprising the steps of
a) providing a recombinant host strain according to the invention, as described above, and
b) incubating said recombinant host strain under fermentation conditions thereby producing phenol.

In a further embodiment of the method according to the invention method, the phenol production can be induced. Such induction of phenol production can be in the absence or in the presence of oxygen ($O_2$). Phenol production can be induced by the presence or the absence of a specific chemical compound or by a change in a physical condition. For instance the presence of an inducer may activate the transcription of certain genes in the biosynthesis pathway to phenol (e.g. IPTG acting on the lac operon to express genes located on a plasmid), or the absence of, for instance, tyrosine may activate the expression of genes involved in the aromatic amino acid pathway from which phenol is derived. A change in a physical condition such as temperature, pH or $O_2$ concentration may also activate the expression of genes involved in phenol synthesis.

In a further embodiment, the method of producing phenol in a recombinant strain can further comprise the step c) of harvesting the produced phenol from the recombinant host strain.

Step b) of the method of producing phenol in a recombinant host according to the invention can be performed as a batch fermentation, as a fed-batch fermentation or as a continuous fermentation.

In the context of the invention, batch fermentation refers to a fermentation method in which the complete fermentation medium is provided at the start of the fermentation. The product is harvested at the end of the fermentation (i.e. phenol).

In the context of the invention, fed-batch fermentation refers to a fermentation method in which a part of the fermentation medium is provided at the start of the fermentation, and a part is fed to the fermenter during the fermentation. The product is harvested at the end of the fermentation (i.e. phenol).

In the context of the invention, continuous fermentation refers to a fermentation method in which substrate is added and the product (i.e. phenol) is removed continuously during the fermentation.

In a further embodiment of the method of producing phenol in a recombinant strain, the fermentation conditions of step b) can comprise aerobic conditions. That means that both the reactions in the shake flasks as well as the fermenter can be performed under aerobic conditions. Such aerobic conditions can be implemented e.g. by gassing the shake flasks and/or fermenter with air.

In a further embodiment of the method of producing phenol in a recombinant strain, the fermentation conditions can comprise the presence of a raw sugar cane juice, wherein said raw sugar cane juice can preferably comprise a high concentration of 1-kestose. One example of this embodiment is shown in Example 6. Such sugar cane juice can be used as the substrate in such fermentation and can comprise, e.g glucose 14 g/l, fructose 24 g/l, sucrose 130 g/l, kestose 119 g/l and nystose 5 g/l, as measured by HPLC.

It will be apparent to those skilled in the art that various modifications can be made to the methods and recombinant host strains of the invention. Thus, it is intended that the present invention covers such modifications and variations, provided they come within the scope of the appended claims and their equivalents.

FIGURES, TABLES AND SEQUENCES

FIG. 1 shows the biosynthesis pathway from glucose to phenol.
E4P=erythrose-4-phosphate
DAHP=3-deoxy-D-arabino-heptulosonate-7-phosphate
3DQ=3-dehydroquinate
3DS=3-dehydroshikimate
SHI=shikimate
SHI3P=shikimate-3-phosphate
ESHI3P=5-enolpyruvyl-shikimate-3-phosphate
CHO=chorismate
4HB=4-hydroxybenzoate
PREPH=prephenate FIG. 2 shows the metabolic engineering by the method of the invention of the cellular reaction network in a host in order to create a recombinant host strain according to the invention that overproduces phenol.

FIG. 6 shows the genes aroG (SEQ ID NO: 9), aroG$^{fbr}$ (SEQ ID NO: 10), aroB (SEQ ID NO: 11), aroL (SEQ ID NO: 12) and ubiC (SEQ ID NO: 1), which were all synthesised with restriction sites (underlined) for BglII and BamHI to allow integration into the plasmid. The ATG start codon and the TAA stop codon are in bold. The G to A feedback resistance mutation in aroG$^{fbr}$ (SEQ ID NO: 10) is bold and underlined.

FIG. 7 shows the gene cluster hbdBCD (SEQ ID NO: 2), which was isolated from E. coli O111:B4 and integrated into the same plasmid that is already carrying ubiC by the appropriate restriction enzymes plasmid. The gene cluster has the composition hbdB: 0.6 kbp, hbdC: 1.4 kbp, hbdD: 0.2 kbp, as indicated.

FIG. 8 shows the HPLC analysis of the fermentation broth, as described in Example 3.

FIG. 9 shows the HPLC analysis of the fermentation broth, as described in Example 5.

FIG. 10 shows the HPLC analysis of the fermentation broth of shake flasks, as described in Example 6.

Table 1 shows a list of the E. coli strains, plasmids and genes used according to the invention.

Table 2 shows the results of Example 1 and Example 2.

Figure 2:
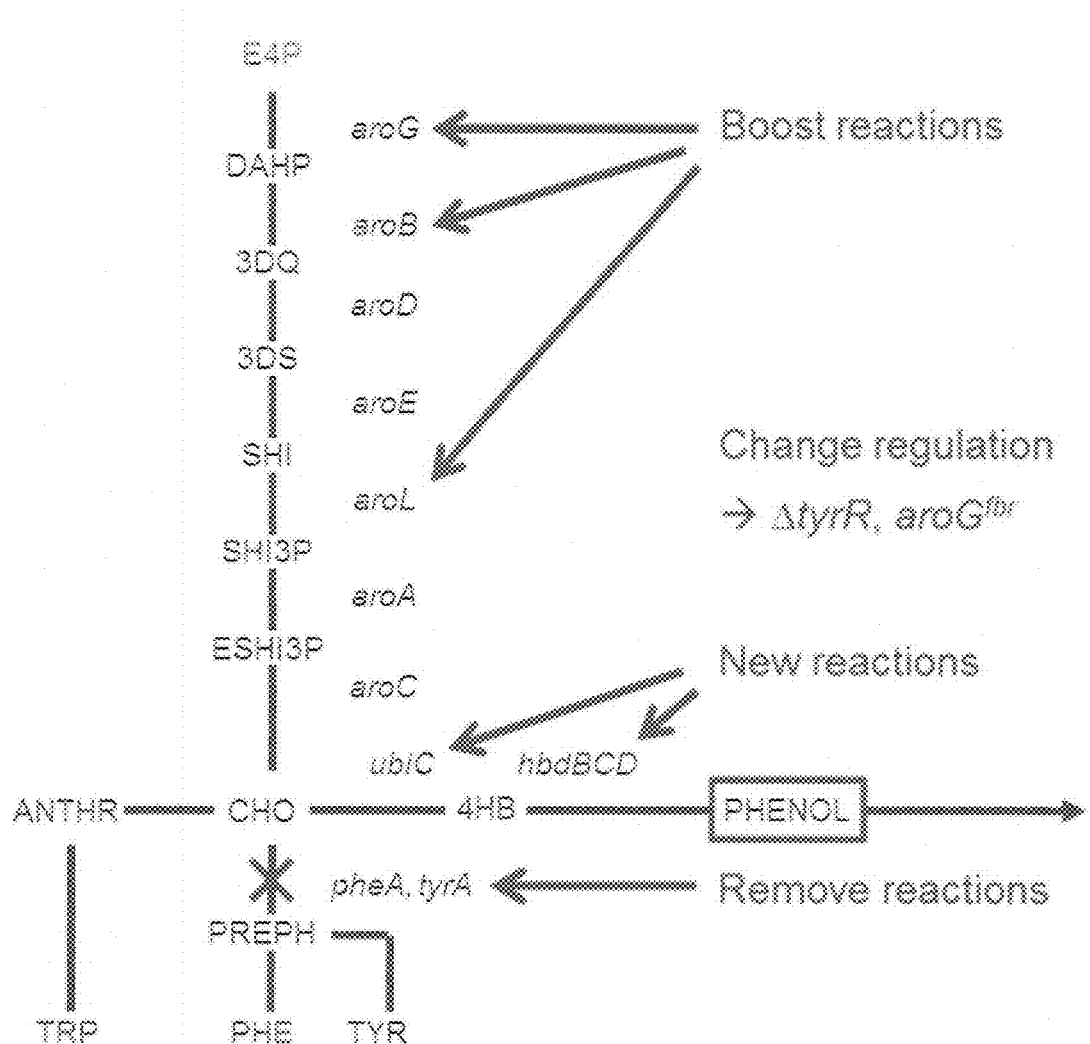

SEQ ID NO: 1 shows the sequence of ubiC. The native gene ubiC, of which this sequence was derived, is found in the NCBI data base under the accession number CP000948, position 4350225 to 4350722. ubiC encodes chorismate lyase, which catalyses the reaction from chorismate (CHO) to 4-hydroxybenzoate (4-HB), as shown in FIG. 2 and in FIG. 3.

Figure 3:
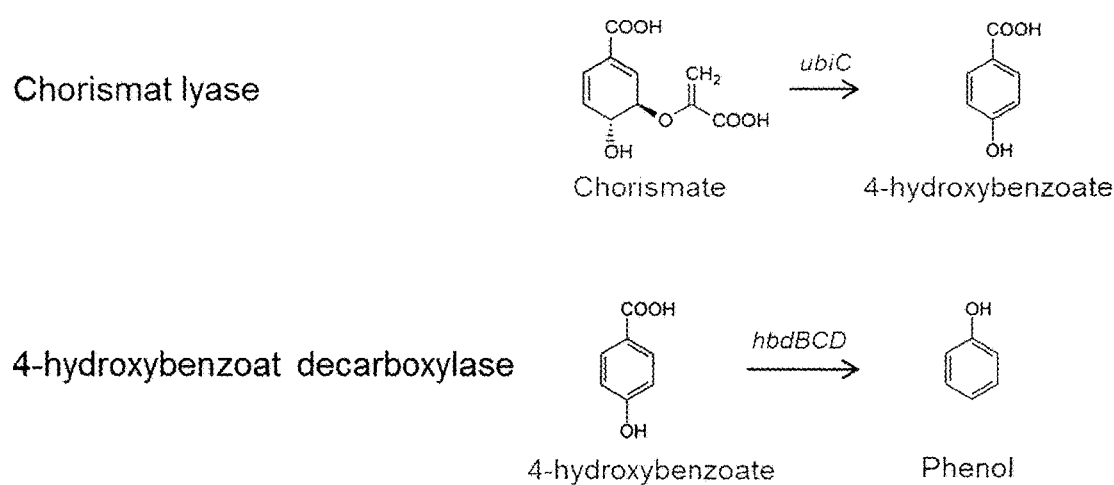
FIG. 3 shows the final two reactions in the phenol synthesis pathway that are catalysed by the ubiC (SEQ ID NO: 1) gene product (CHO to 4-HB) and by the hbdBCD (SEQ ID NO: 2) gene product hydroxybenzoic acid decarboxylase (4-HB to phenol).
Figure 4C:
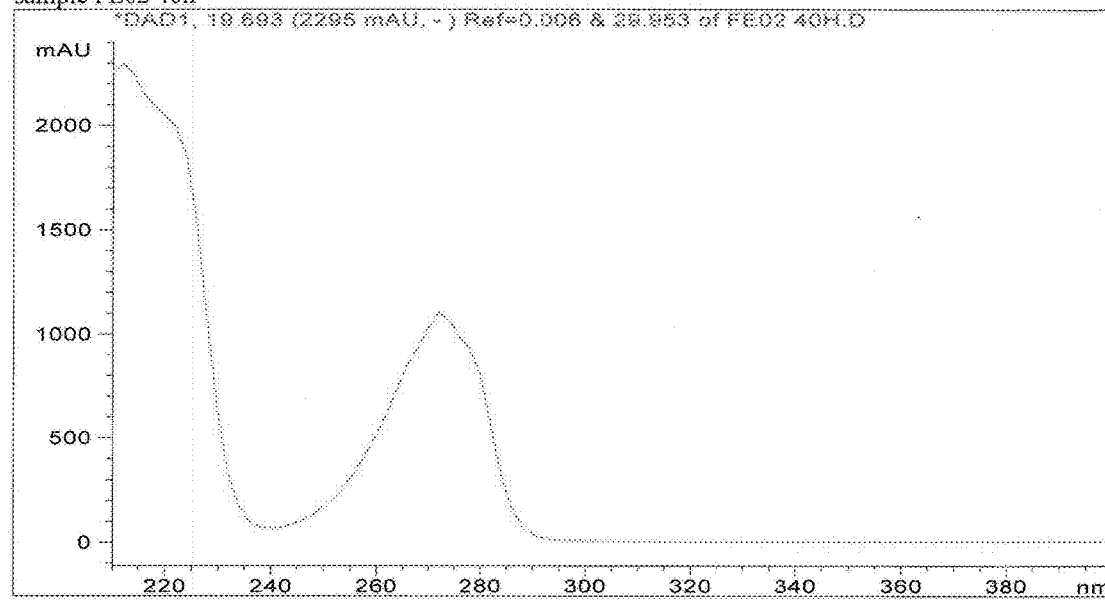
FIG. 4 shows the HPLC analysis of the fermentation broth, as described in Example 1.
Figure 4D:
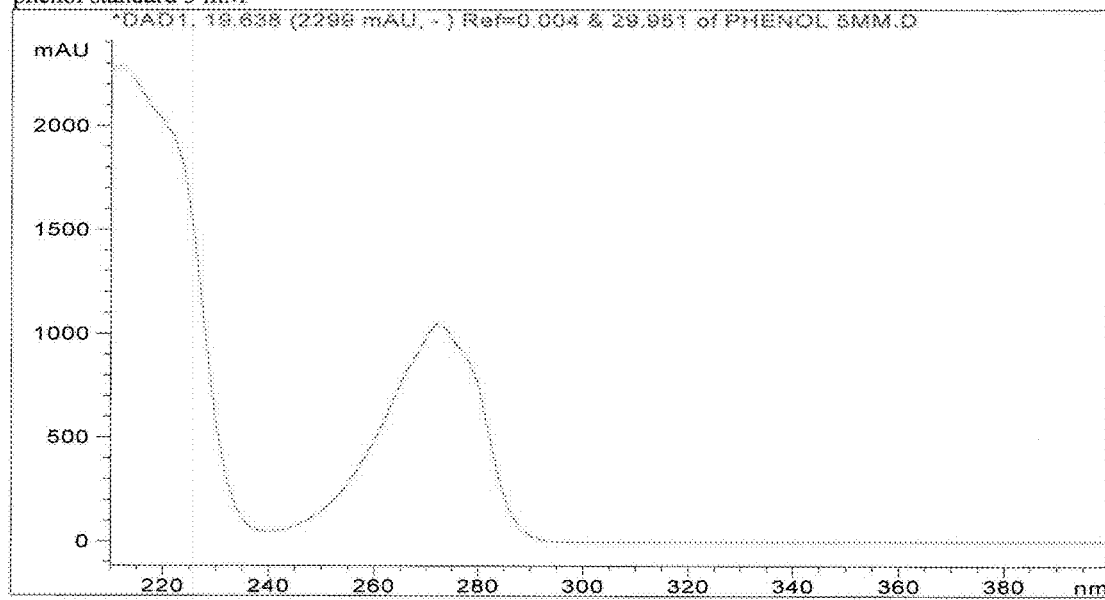
Figure 4E:
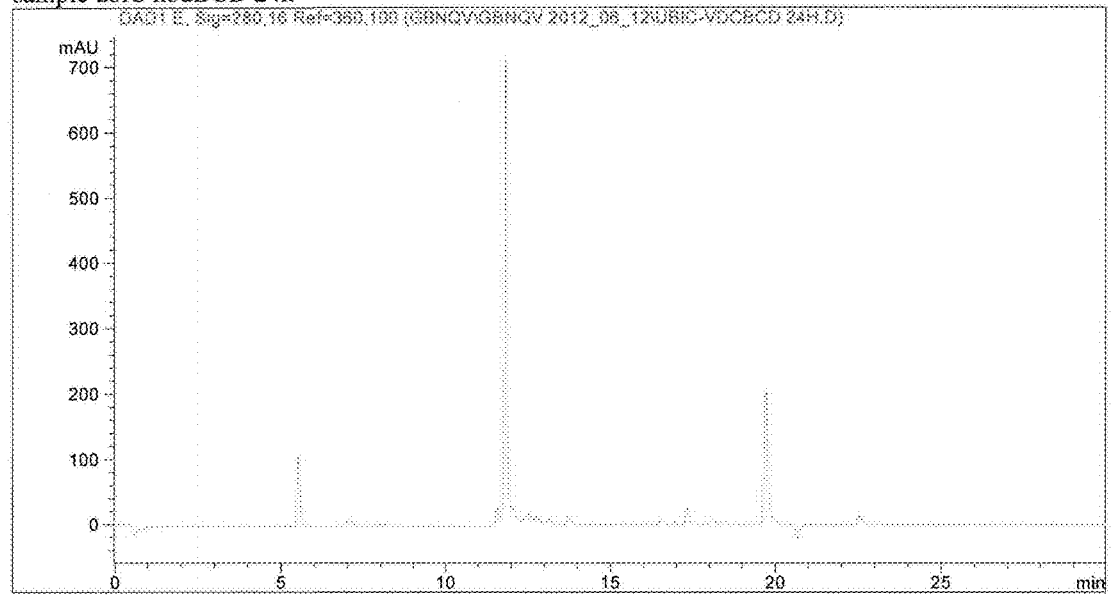
Figure 4F:
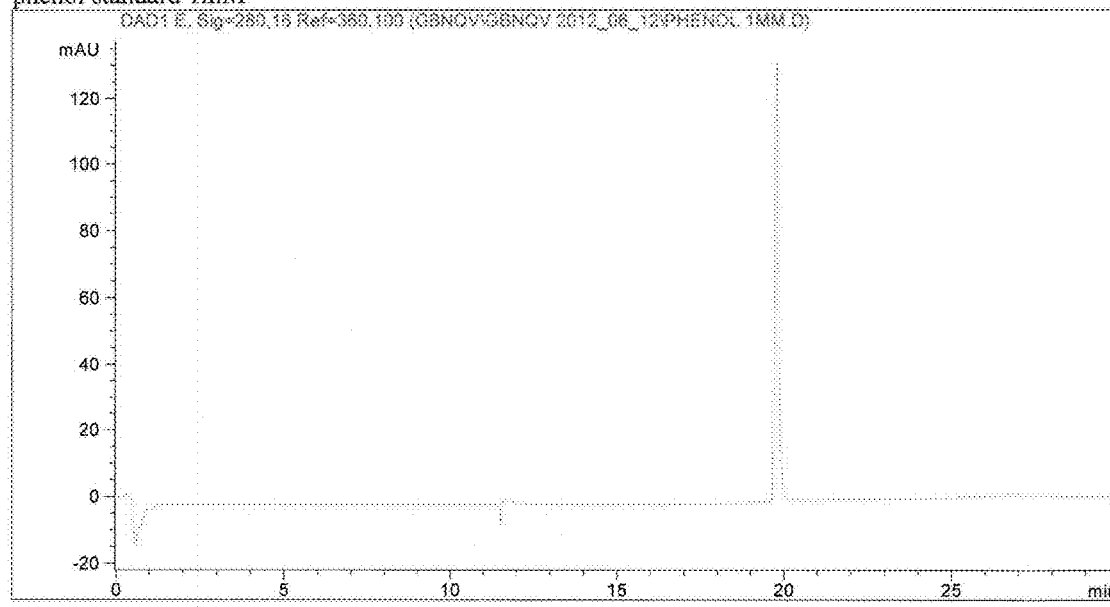
Figure 4G:
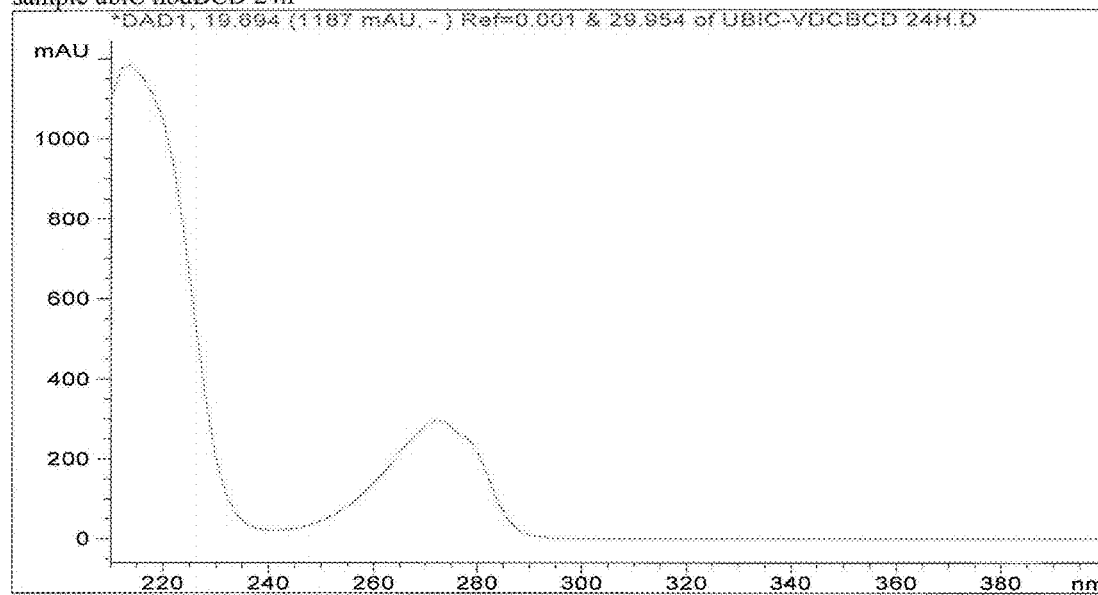
Figure 4H:
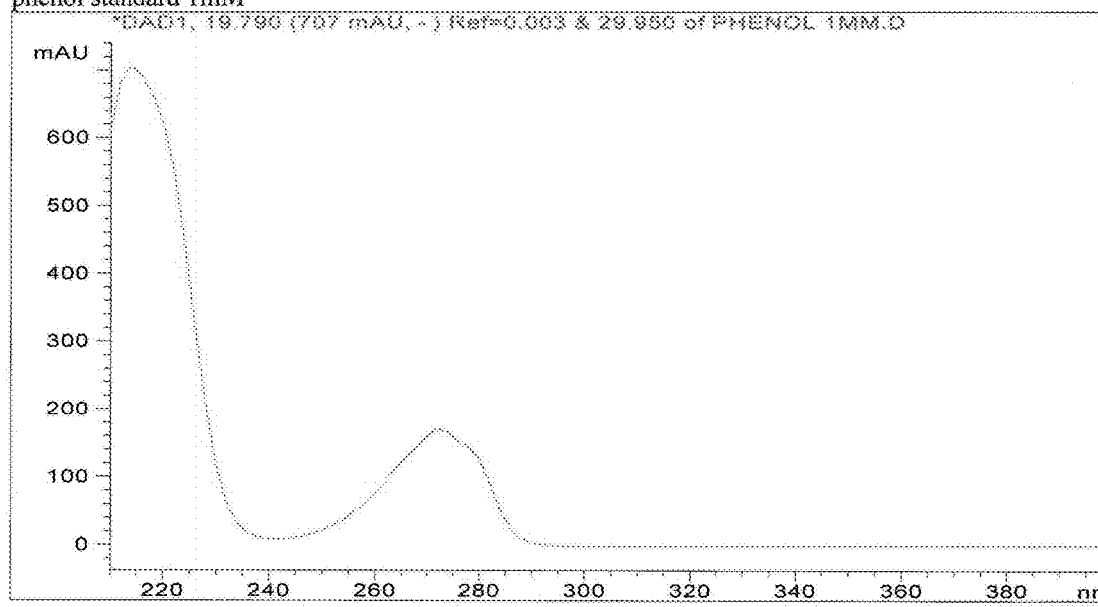
Figure 5A:
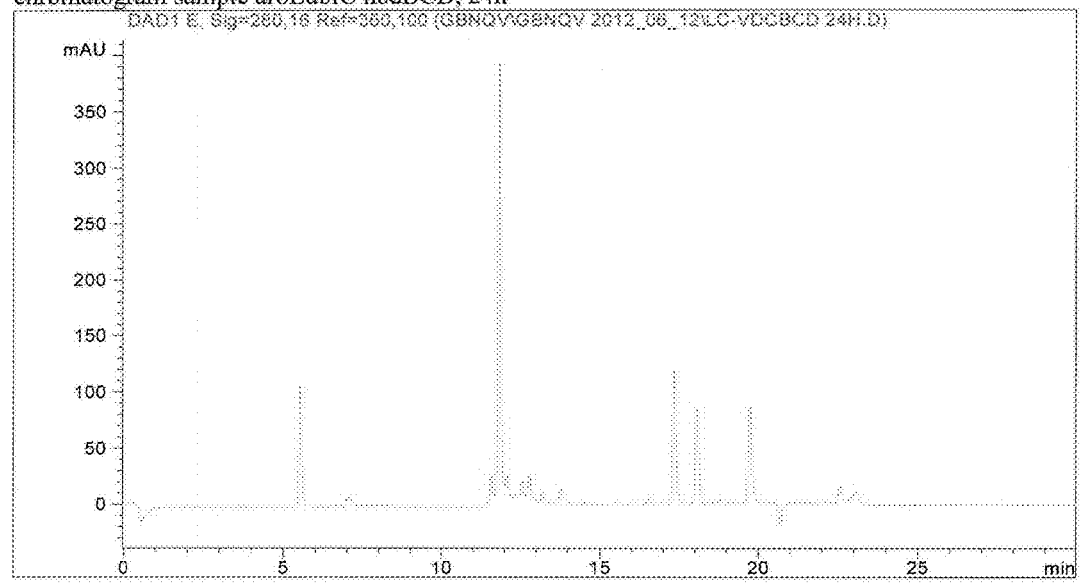
FIG. 5 shows the HPLC analysis of the fermentation broth, as described in Example 2.
Figure 5B:
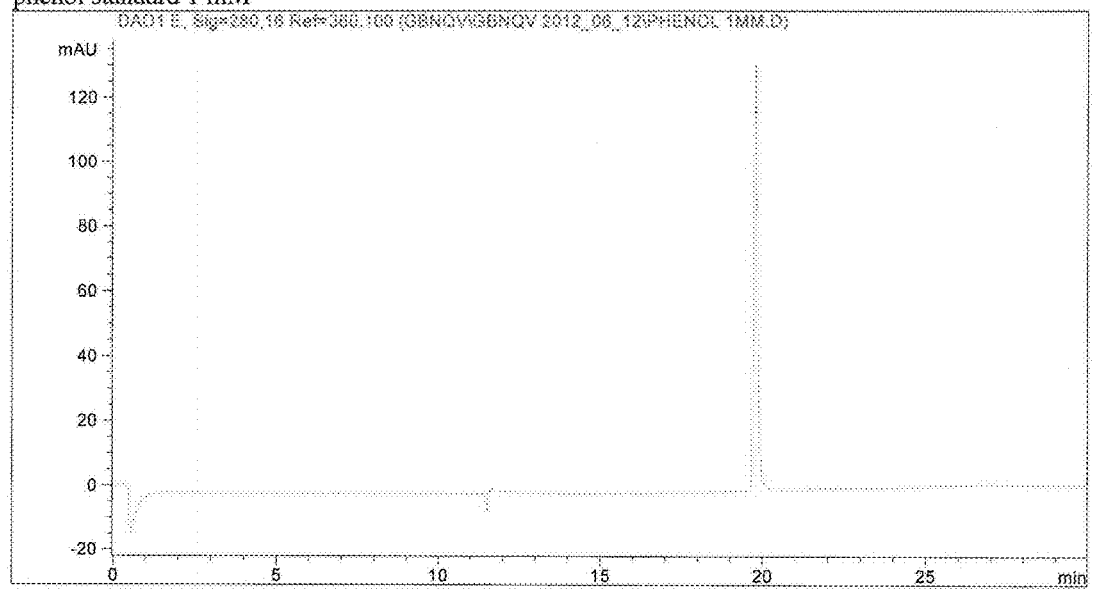
Figure 5C:
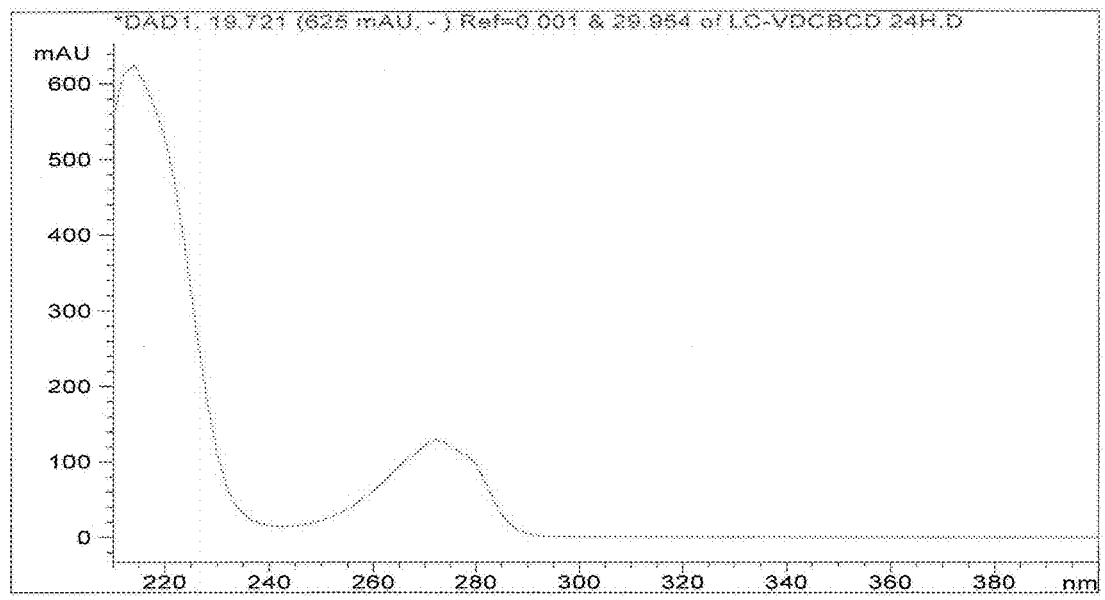
Figure 5D:
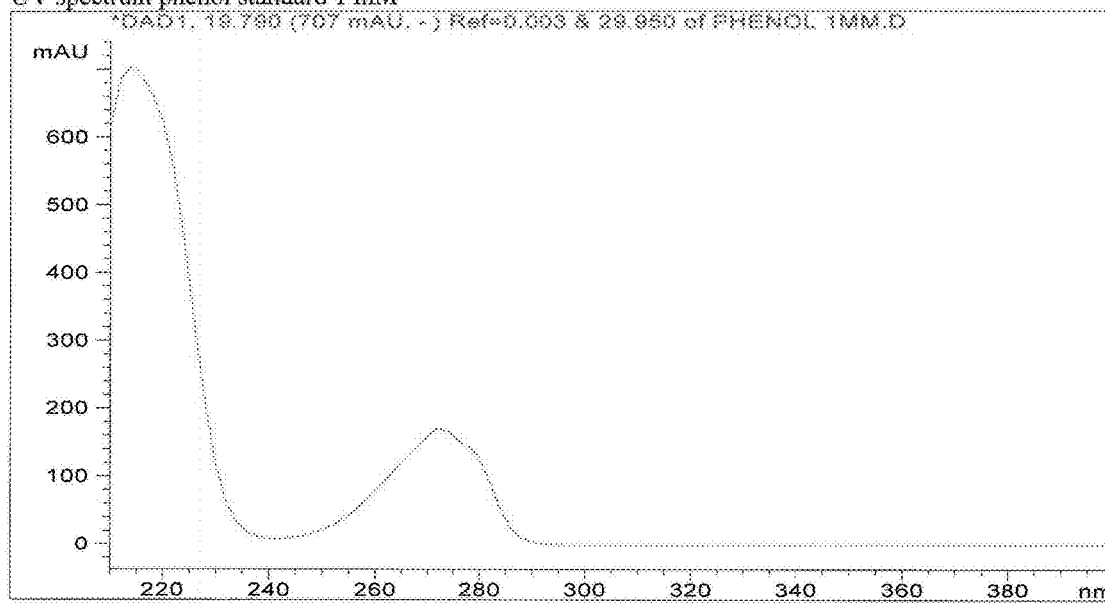
Figure 8A:
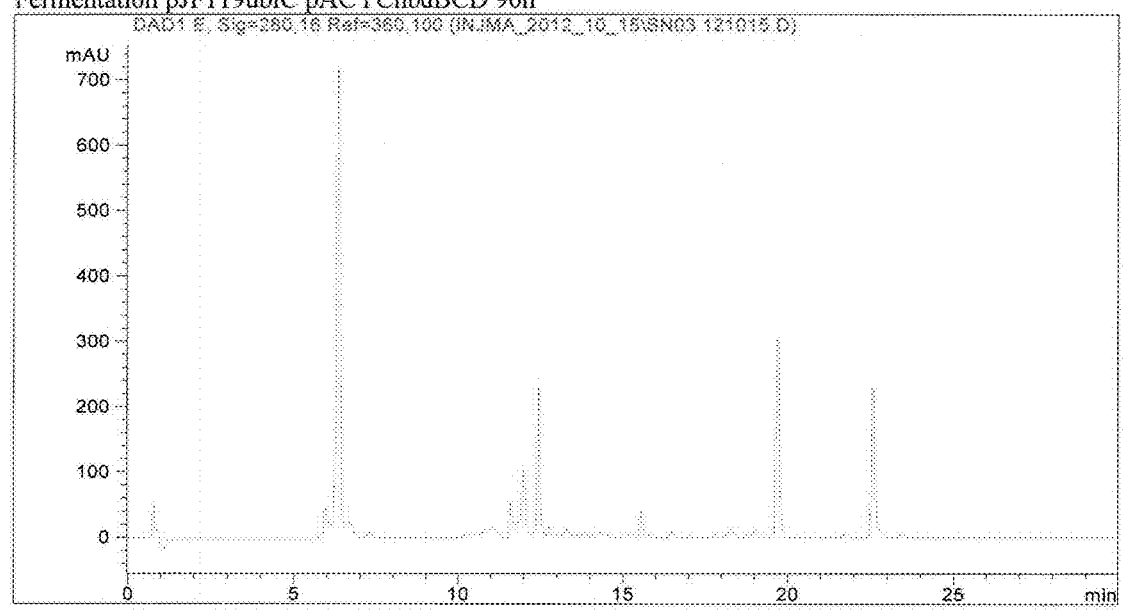
Figure 8B:
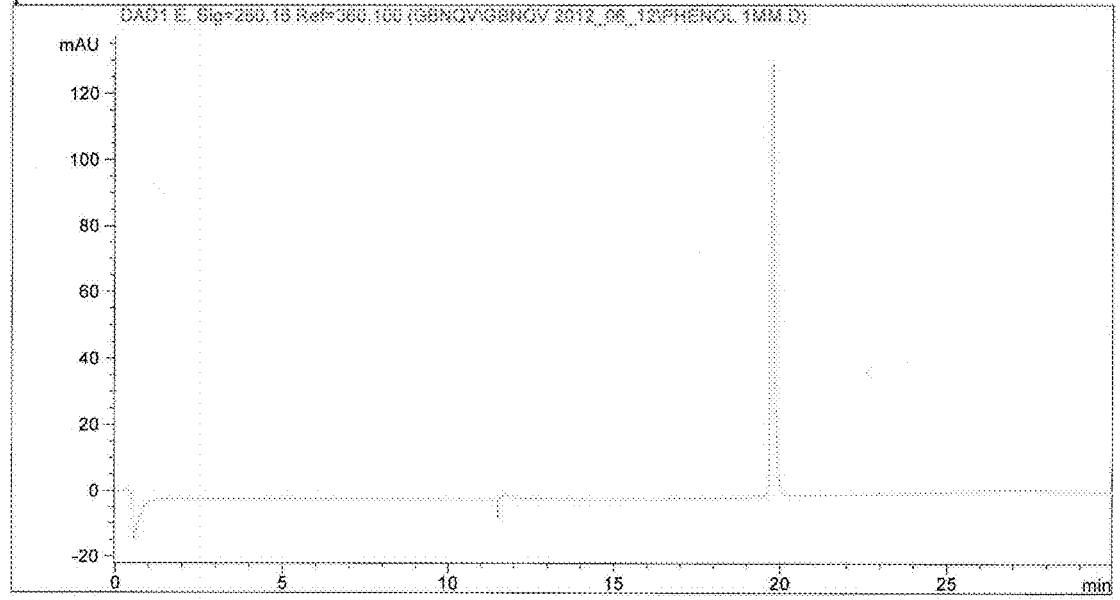
Figure 8C:
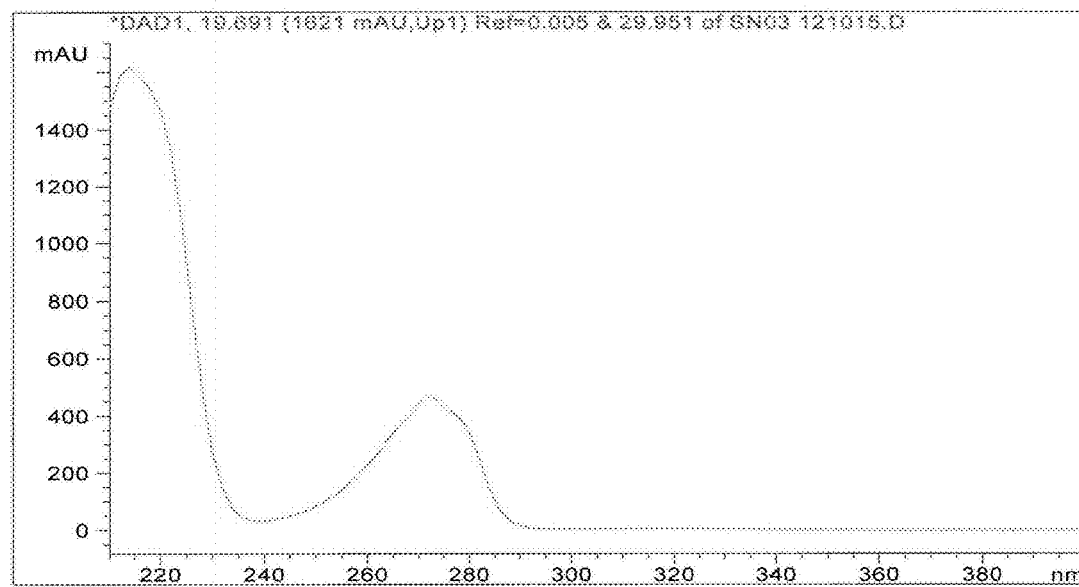
Figure 8D:
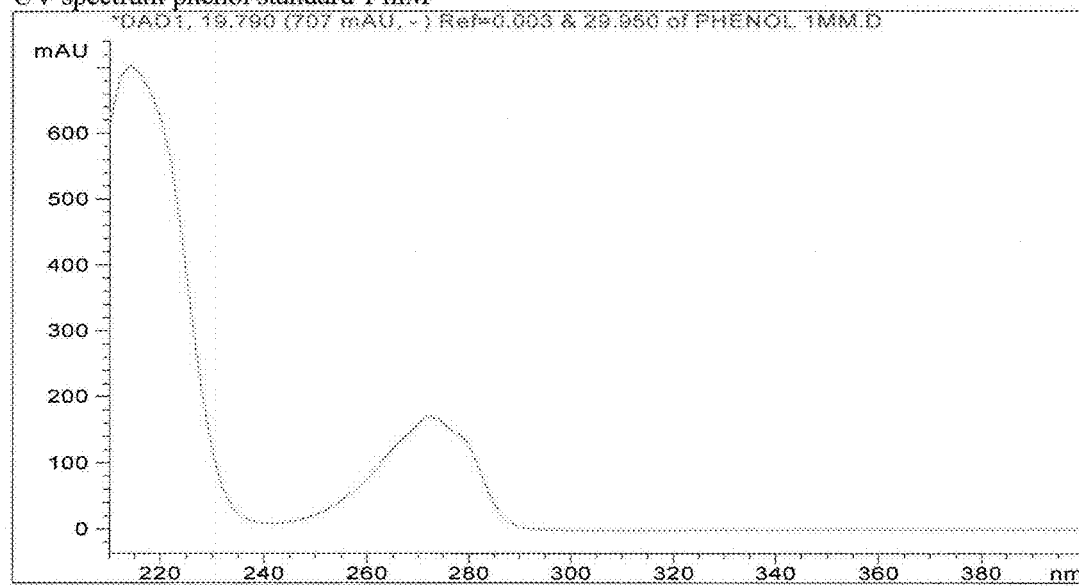

SEQ ID NO: 2 shows the sequence of the gene cluster hbdBCD derived from E. coli O111:B4. The gene cluster has the composition hbdB: 0.6 kbp, hbdC: 1.4 kbp, hbdD: 0.2 kbp, as depicted in FIG. 7. The sequence can be found in the NCBI data base under the accession number NC_013364 position 3434167 to 3431906. The gene cluster encodes 4-hydroxybenzoate decarboxylase that catalyses the reaction from 4-hydroxybenzoate (4-HB) to phenol, as shown in FIG. 2 and FIG. 3.

SEQ ID NO: 3 shows the sequence of the tyrR::FRT-kan cassette, which was used to delete tyrR.

SEQ ID NO: 4 shows the sequence of the pheAtyrA:: FRT-CAT cassette, which was used to delete pheAtyrA.

SEQ ID NO: 5 shows the sequence of the knockout primer tyrR, the 5' primer, which as used for deleting tyrR.

SEQ ID NO: 6 shows the sequence of the knockout primer tyrR, the 3' primer, which as used for deleting tyrR.

SEQ ID NO: 7 shows the sequence of the knockout primer pheAtyrA, the 5' primer, which as used for deleting pheAtyrA.

SEQ ID NO: 8 shows the sequence of the knockout primer pheAtyrA, the 3' primer, which as used for deleting pheAtyrA.

SEQ ID NO: 9 shows the sequence of aroG. The native gene aroG, of which this sequence was derived, is found in the NCBI data base under the accession number CP000948, position 837448 to 838500. The aroG gene product which catalyses the reaction from E4P to DAHP, as shown in FIG. 2.

SEQ ID NO: 10 shows the sequence of aroG$^{fbr}$. The sequences as per SEQ ID NO: 7 differs from SEQ ID NO: 9 by the fact that G is changed to A at position 436, thereby generating the fbr (feedback resistance) mutant of aroG.

SEQ ID NO: 11 shows the sequence of aroB. The native gene aroB, of which this sequence was derived, is found in the NCBI data base under the accession number CP000948, position 3613165 to 3614253. The aroB gene product catalyses the reaction from DAHP to 3DQ, as shown in FIG. 2.

SEQ ID NO: 12 shows the sequence of aroL. The native gene aroL, of which this sequence was derived, is found in the NCBI data base under the accession number CP000948, position 344960 to 345484. The aroL gene product catalyses the reaction from SHI to SHI3P, as shown in FIG. 2.

SEQ ID NO: 13 shows the sequence of an insertion cassette with a Ptac promotor and a ribosome binding site upstream of the aroBaroG$^{fbr}$ sequence, and a FRT flanked chloramphenicol resistance downstream of the aroBaroG$^{fbr}$ sequence as well as a transcription terminator, as described in Example 5.

SEQ ID NO: 14 and SEQ ID NO: 15 show the sequences of the amplification primer pair that was used to amplify the insertion cassette, as shown in SEQ ID NO: 13.

SEQ ID NO: 16 shows the sequence of the cloning site on the chromosome after integration of the cassette in the fuc locus between the fucP and fucI genes, as described in Example 5. This sequence includes the chromosomal DNA sequences directly upstream and downstream of the cassette. The cassette is found between position 5148 and 9112 of SEQ ID NO: 16.

SEQ ID NO: 17 and SEQ ID NO: 18 show the sequence of the primer pair used for testing for successful chromosomal integration of the cassette, as described in Example 5. Mutants with defects in the fuc locus are not able to grow on L-fucose as a carbon source and will form pale colonies on MacConkey medium containing 1% fucose (contrary to wild type cells which will form red colonies, as described by Albermann et al. 2010). After selection on agar plates containing chloramphenicol, the positive colonies were further tested on MacConkey medium with 1% fucose. The fucose negative colonies were further tested with by PCR using primers SEQ ID NO: 17 for the 5'-test and SEQ ID NO 18 for the 3'-test.

EXAMPLES

Example 1

Figure 1:
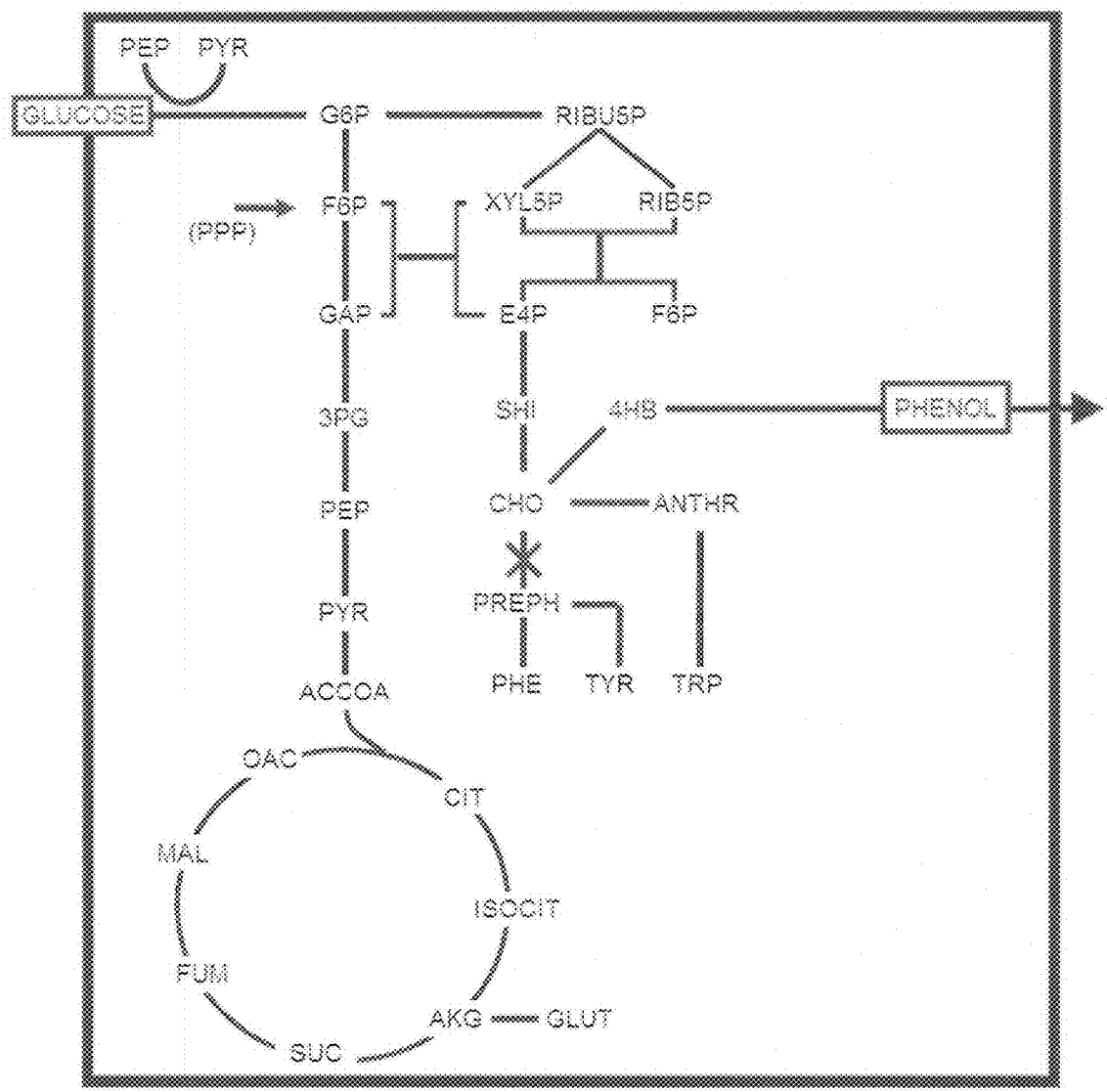

Creating the Recombinant Strain *E. coli* BW25113 ΔtyrR ΔpheAtyrA pJF119ubiChbdBCD and Using it for Phenol Production by Fermentation A novel biosynthesis pathway for synthesizing phenol from sugar via chorismate (CHO) was identified (see FIG. 1 and FIG. 2). This pathway was implemented in an *E. coli* strain and the further genetic modifications necessary to create a phenol producing strain were performed (see FIG. 2). In this way the whole cell biosynthesis of phenol was made possible. The created recombinant strain produced between 0.5 mM and 1.5 mM phenol in shake flask experiments and up to 5 mM in a 1 liter bioreactor fermentation. A list of the *E. coli* strains, plasmids and genes used is provided in Table 1.

The following genetic modifications were performed to overproduce chorismate in addition to the endogenous chorismate of the host strain *E. coli* BW25113: the genes pheA and tyrA were deleted in order to remove the chorismate mutase reaction that consumes chorismate so that chorismate is overproduced. These deletions make the strain auxotrophic towards phenylalanine and tyrosine. In addition, the regulatory gene tyrR that encodes an aporepressor for the expression of the Tyr regulon was deleted. The corepressor of tyrR is either tyrosine or phenylalanine plus tryptophan.

a. Creating the Host Strain *E. coli* BW25113 dtyrR dpheAtyrA

The knock out deletion of the genes pheA, tyrA and tyrR genes was performed by using recombination by the phage λ red recombinase according to the method of Datsenko and Wanner (Datsenko, K. A., Wanner, B. L., One-step inactivation of chromosomal genes in *Escherichia coli* K-12 using PCR products (2000), PNAS, 97 6640-6645). pheA and tyrA are located right next to each other on the chromosome and were inactivated in one step. tyrR is located on a different place on the chromosome and was inactivated in a second step by the same method.

The insertion cassettes used for the disruptions contained an antibiotic resistance gene flanked by FRT (flippase recognition target) sites. Sequences homologous to regions adjacent to the gene to be inactivated were located at either end of the cassettes as described by Datsenko and Wanner. The insertion cassettes were amplified by PCR (polymerase chain reaction) from template plasmids with the antibiotic resistance gene and the FRT sites. The PCR primers contained the homologous regions and a priming site. The insertion cassette pheAtyrA::FRT-CAT used for pheAtyrA disruption had a chloramphenicol resistance and is given by SEQ ID NO: 4. The primers used for the amplification of the pheAtyrA knockout cassette (pheAtyrA::FRT-CAT cassette, SEQ ID NO: 4) are given by SEQ ID NO: 7 and SEQ ID NO: 8. The plasmid pCO1-FRT-CAT was used as template plasmid for the pheAtyrA::FRT-CAT cassette. The insertion cassette tyrR::FRT-kan used for tyrR disruption had a kanamycin resistance and is given by SEQ ID NO: 3. The primers used for the amplification of the tyrR knockout cassette (tyrR::FRT-kan, SEQ ID NO: 3) are given by SEQ ID NO: 5 and SEQ ID NO: 6. The plasmid pCO1-FRT-kan was used as template plasmid for the tyrR::FRT-kan cassette.

The tyrR::FRT-kan cassette was integrated into the chromosome of *E. coli* BW25113 by the λ red recombinase, thus yielding the strain *E. coli* BW25113 ΔtyrR. Cells in which the disruption had been successful were selected on agar plates containing kanamycin. Furthermore, control PCR was carried out to demonstrate the successful disruption. In the same way, the cassette pheAtyrA::FRT-CAT was integrated into the chromosome of *E. coli* BW25113 ΔtyrR by the λ red recombinase, thus yielding the strain *E. coli* BW25113 ΔtyrR ΔpheAtyrA (see Table 1). Cells in which the disruption had been successful were selected on agar plates containing chloramphenicol. Control PCR was again used to demonstrate the successful disruption of pheAtyrA. In addition, the phenylalanine and tyrosine auxotrophy of the created mutants was checked. The mutants were only able to grow in the presence of phenylalanine and tyrosine. In both chromosomal integrations the helper plasmid pKD46 was used to express the λ red recombinase. The antibiotic resistances were removed from *E. coli* BW25113 ΔtyrR ΔpheAtyrA by expressing a flippase using the helper plasmid pCP20.

b. Creating the Strain *E. coli* BW25113 dtyrR dpheAtyrA pJF119ubiChbdBCD

The plasmid pJF119 (Fürste, J. P., Pansegrau, W., Frank, R., Blocker, H., Scholz, P., Bagdasarian, M., Lanka, E. (1986) Molecular Cloning of the Plasmid RP4 Primase Region in a Multi-Host-Range tacP Expression Vector. Gene 48 119-131) was chosen as a vector for the over-expression of ubiC and hbdBCD.

The gene ubiC was designed with 5' restriction sites for NdeI and BglII and 3' restriction site for BamHI and synthesized by the company Geneart (part of Life Technologies). The delivery plasmid pMA was amplified in *E. coli* DH10b and the gene cut off by NdeI and BamHI restriction enzymes. Preparative agarose gel electrophoresis was used to purify the gene. A cloning site on pJF119 was opened by a sequential digest with first NdeI and then BamHI. The ubiC gene and the vector were ligated by T4 ligase (see FIG. 6 and SEQ ID NO: 1). The successful integration of the ubiC gene on the pJF119 plasmid was checked by digesting pJF119ubiC by NdeI/BamHI digestion and analyzing the DNA fragments by agarose gel electrophoresis. The protein expression profile was checked by expressing pJF119ubiC in *E. coli* DH10b and subsequent SDS-PAGE analysis of the cell extract. The activity of the gene product UbiC was demonstrated by incubating raw enzyme extracts of *E. coli* DH10b pJF119ubiC with chorismate and measuring the resulting 4-hydroxybenzoate production by HPLC. Finally, the plasmid pJF119ubiC was sequenced by the company Qiagen and the detected sequence was aligned to the original ubiC gene sequence and controlled for homology. All analyses confirmed the successful integration of ubiC into pJF119.

The gene cluster hbdBCD was amplified by PCR from the chromosome of the strain E. coli O111:B4 (ATCC 33780) using primers with restriction sites for HindIII/EcoRI. The primer product was then incorporated on the plasmid pUC19 by digesting pUC19 with HindIII/EcoRI and ligating the primer product with the opened pUC19 using T4 ligase (see FIG. 7 and SEQ ID NO: 2).

The plasmid pUC19hbdBCD was then digested with DrdI. The resulting DNA fragment of approx. 3 kb contained the hbdBCD gene cluster. This fragment was purified by preparative agarose gel electrophoresis. The fragment was incorporated into pJF119ubiC by digesting this vector with DrdI and ligating the fragment with the vector using T4 ligase. The correct cloning of hbdBCD was checked by digesting pJF119ubiChbdBCD with bglII and RsrII and separating the resulting fragments using agarose gel electrophoresis. The observed bands matched the expected DNA fragments. The activity of the gene product HbdBCD was demonstrated by incubating raw enzyme extracts of E. coli DH10b pJF119hbdBCD with 4-hydroxybenzoate and measuring the resulting phenol production by HPLC.

The pJF119 plasmid contains an ampicillin resistance which is used for selection. A second variant of the plasmid pJF119ubiChbdBCD was made by exchanging the ampicillin resistance for a kanamycin resistance. This was done by digesting pJF119hbdBCD with BspHI to remove the ampicillin resistance and then ligating the linear pJF119hbdBCD fragment with a gene for kanamycin resistance.

Finally, pJF119ubiChbdBCD was transferred into E. coli BW25113 ΔtyrR ΔpheAtyrA by electroporation to create the strain E. coli BW25113 ΔtyrR ΔpheAtyrA pJF119ubiChbdBCD (see Table 1). Both a variant with ampicillin resistance on the plasmid as well as a variant with kanamycine resistance on the plasmid was created.

c. Producing phenol from sugar with the strain E. coli BW25113 ΔtyrR ΔpheAtyrA pJF119ubiChbdBCD E. coli BW25113 ΔtyrR ΔpheAtyrA pJF119ubiChbdBCD with ampicillin resistance was grown in a 10 ml shake flask culture and in a 1 l bioreactor/fermenter, both under aerobic conditions. Such aerobic conditions were implemented by gassing the shake flask and/or bioreactor/fermenter with air.

The fermentation medium used for the shake flask culture was based on an E. coli medium published by Riesenberg et al (Riesenberg D., Schulz V., Knorre, W. A., Pohl, H-D., Korz, D., Sanders E. A., Ro, A., Deckwer, W-D. (1991) High cell density cultivation of Escherichia coli at controlled specific growth rate. Journal of Biotechnology 20 17-27). It contained the following compounds: 13.3 g/L $KH_2PO_4$, 4 g/L $(NH_4)_2PO_4$, 1.7 g/L Citrate, 2.5 g/l Luria Broth, 17.5 g/L Glucose, 0.024 g/L L-Phenylalanine, 0.016 g/L L-Tyrosine, 10 ml/l trace element solution, 0.6 g/L $MgSO_4*7\ H_2O$, 0.2 mM $CaCl_2*2\ H_2O$, 0.1 g/l ampicillin The fermentation medium used in the bioreactor contained the following components: 15.5 g/L $KH_2PO_4$, 4.67 g/L $(NH_4)_2PO_4$, 1.98 g/L Citrate, 17.5 g/L Glucose, 0.5 g/L Thiamine, 0.037 g/L L-Phenylalanine, 0.024 g/L L-Tyrosine, 10 ml/l trace element solution, 0.6 g/L $MgSO_4*7\ H_2O$, 0.2 mM $CaCl_2*2\ H_2O$, 0.1 g/l ampicillin The trace element solution had the following composition: 75 mg/L Fe(III)Citrat*H2O. 3.75 mg/L $H_3BO_3$, 18.75 mg/L $Mn(II)Cl_2*4\ H_2O$, 10.5 mg/L EDTA (Titriplex III), 1.88 mg/L $CuCl2*2\ H_2O$, 3.13 mg/L $Na_2MoO_4*2\ H_2O$, 3.13 mg/L $Co(II)Cl_2*6\ H_2O$, 10 mg/L Zn Acetate*2$H_2$O.

In the bioreactor the concentration of dissolved oxygen was controlled at $pO_2$=5% and the pH was controlled at pH=7.0 by addition of a 25% $NH_4$ solution. That means that aerobic conditions were used, wherein the aerobic conditions were implemented e.g. by gassing the shake flasks and/or fermenter/bioreactor with air.

The expression of the genes on pJF119 was induced by adding IPTG to the culture once the bacteria had reached their exponential growth phase.

As a negative control shake flask fermentations were performed with the strains E. coli BW25113 ΔtyrR ΔpheAtyrA pJF119Δ and E. coli BW25113 ΔtyrR ΔpheAtyrA pUC19hbdBCD. pJF119Δ signifies a pJF119 plasmid without any added genes. The same shake flask fermentation medium was used for the negative controls and the fermentation procedure was identical including the addition IPTG.

The shake flask fermentation with E. coli BW25113 ΔtyrR ΔpheAtyrA pJF119ubiChbdBCD yielded 1.4 mM phenol after 24 hours. The fermentations in the bioreactor yielded 4.9 mM phenol after 40 hours. No phenol could be detected in the cultures of the negative controls (see Table 2). The concentrations were determined by HPLC-UV using a gradient method of 30 minutes and UV detection at 280 nm. The phenol peaks in the samples had identical retention times and UV-spectra to a phenol standard solution (see FIG. 4). HPLC-MS was used to detect the mass of phenol as a further confirmation of phenol production (see Table 2).

Example 2

Creating the Recombinant Strain E. coli BW25113 ΔtyrR ΔpheAtyrA pJF119aroLubiChbdBCD and Using it for Phenol Production by Fermentation The host strain E. coli BW25113 ΔtyrR ΔpheAtyrA was developed as described in Example 1.

The gene aroL (SEQ ID NO: 12) was designed with a 5' restriction sites for NdeI and BglII and 3' restriction site for BamHI and synthesized by the company Geneart (part of Life Technologies), see also FIG. 6. It was then cloned in the plasmid pJF119 by the same method as described for the cloning of ubiC in Example 1 to create the plasmid pJF119aroL (see Table 1).

ubiC (SEQ ID NO: 1) was cloned onto the created plasmid pJF119aroL downstream of the aroL gene. pJF119aroL was digested with BamHI and ubiC was then cut off the delivery plasmid by digesting with BglII and BamHI. ubiC was ligated with the opened vector using T4 ligase to yield the plasmid pJF119aroLubiC. The correct integration of aroL and ubiC on pJF119 was checked by digesting with NdeI. This yielded two fragments; the aroL gene (0.5 kb) and the vector with ubiC (5.8 kb). A wrong orientation of ubiC would yield different fragments. One fragment would be the entire insert aroLubiC (1.0 kb) and the other the vector without insert (5.3 kb). The insert was also sequenced by Qiagen and the result aligned to the expected sequence. Both analyses confirmed the correct integration of aroL and ubiC in pJF119.

The hbdBCD gene cluster (SEQ ID NO: 2) was cloned on the pJF119aroLubiC plasmid by the method described in Example 1 and transformed into the strain E. coli BW25113 ΔtyrR ΔpheAtyrA to create E. coli BW25113 ΔtyrR ΔpheAtyrA pJF119aroLubiC (see Table 1).

The fermentation with E. coli BW25113 ΔtyrR ΔpheAtyrA pJF119aroLubiC was done in a shake flask using the same method and the same fermentation medium as described above in Example 1.

This shake flask fermentation yielded 0.59 mM phenol after 24 hours. No phenol could be detected in the cultures of the negative controls (see Table 2). The concentrations were determined by HPLC-UV using a gradient method of 30 minutes and UV detection at 280 nm. The phenol peaks in the samples had identical retention times and UV-spectra to a phenol standard solution (see FIG. 5). HPLC-MS was used to detect the mass of phenol as a further confirmation of phenol production (see Table 2).

Example 3

Creating the Recombinant Strain E. coli BW25113 ΔtyrR ΔpheAtyrA pJF119ubiC pACYChbdBCD and Using it for Phenol Production by Fermentation The strain E. coli BW25113 ΔtyrR ΔpheAtyrA pJF119ubiC was created as described in Example 1.

The gene cluster hbdBCD was amplified by PCR from the chromosome of the strain E. coli O111:B4 (ATCC 33780) and cloned on plasmid pUC19 as described in Example 1. The plasmid pUC19hbdBCD was digested with EcoRI and HindIII to release the hbdBCD gene cluster. This DNA fragment was purified by preparative agarose gel electrophoresis. The plasmid pACYC was digested with EcoRI and HindIII. The linearized vector was purified by preparative agarose gel electrophoresis and ligated with the hbdBCD fragment. The resulting plasmid pACYC hbdBCD was transformed into E. coli DH10b and selected on agar plates containing chloramphenicol (pACYC contains a chloramphenicol resistance). The correct incorporation of hbdBCD on pACYC was controlled by digesting with EcoRI and HindIII and analysing the resulting fragments by agarose gel electrophoresis. This analysis confirmed the correct cloning of hbdBCD on pACYC. The plasmid pACYChbdBCD was transformed into the strain E. coli BW25113 ΔtyrR ΔpheAtyrA and a control digestion with EcoRI and HindIII was repeated with plasmid from the transformed strain. This analysis again confirmed the correct cloning of hbdBCD on pACYC. The plasmid pJF119ubiC, described in Example 1, was transformed into E. coli BW25113 ΔtyrR ΔpheAtyrA pACYChbdBCD to yield the strain E. coli BW25113 ΔtyrR ΔpheAtyrA pJF119ubiC pACYChbdBCD.

A fermentation with E. coli BW25113 ΔtyrR ΔpheAtyrA pJF119ubiC pACYChbdBCD was performed in a 1 liter bioreactor. The procedure and the fermentation medium was the same as described in Example 1 with the exception that the fermentation medium contained 0.1 g/l carbenicillin and 0.05 g/l chloramphenicol instead of ampicillin.

This bioreactor fermentation yielded 2.3 mM phenol after 90 hours. No phenol could be detected in the cultures of the negative controls (see Table 2). The concentrations were determined by HPLC-UV using a gradient method of 30 minutes and UV detection at 280 nm. The phenol peaks in the samples had identical retention times and UV-spectra to a phenol standard solution (see FIG. 8). HPLC-MS was used to detect the mass of phenol as a further confirmation of phenol production (see Table 2).

Example 4

Creating the Recombinant Strain E. coli BW25113 ΔtyrR ΔpheAtyrA pJF119hbdBCDubiC and Using it for Phenol Production by Fermentation In Example 1 the hbdBCD gene cluster was located downstream of the ubiC gene and had its own lac promoter. The ubiC gene had a tac promoter. In this example the hbdBCD gene cluster was moved to a position just before the ubiC gene, right after its tac promoter so that both the hbdBCD and the ubiC gene were expressed by the tac promoter.

hbdBCD was cut from the pJF119ubiChbdBCD construct described in Example 1 with the restriction enzymes NdeI and HindIII and purified by preparative agarose gel electrophoresis. The pACYC plasmid was cut with the same restriction enzymes, dephosphorylated and ligated with the hbdBCD gene yielding the construct pACYChbdBCD.

The construct pACYChbdBCD was then digested with EcoRI to release the hbdBCD gene with EcoRI overhangs. The construct pJF119ubiC described in Example 1 was digested with EcoRI, dephosphorylated and ligated with the hbdBCD gene to yield the construct pJF119hbdBCDubiC. The expression of hbdBCD after induction with IPTG was demonstrated by agarose gel electrophoresis.

The plasmid construct pJF119hbdBCDubiC was transformed in the strain BW25113 ΔtyrR ΔpheAtyrA described in Example 1. A shake flask fermentation with IPTG induction performed according to the method described in Example 1 yielded 0.093 mM phenol.

Example 5

Creating the Recombinant Strain E. coli BW25113 ΔpheAtyrA ΔtyrR Fuc::$P_{tac}$aroBaroG$^{fbr}$ pJF119ubiChbdBCD and Using it for Phenol Fermentation The genes aroB (sequence number) and aroG$^{fbr}$ (sequence number) were integrated on the chromosome of the strain E. coli BW25113 ΔpheAtyrA ΔtyrR using an insertion cassette with a Ptac promoter and a ribosome binding site upstream of the aroBaroG$^{fbr}$ sequence, and a FRT flanked chloramphenicol resistance downstream of the aroBaroG$^{fbr}$ sequence as well as a transcription terminator (chromosomal integration). The sequence for the insertion cassette is given by SEQ ID NO: 13. The sequence for the primers used to amplify the insertion cassette is given by SEQ ID NO: 14 (5'-TGC TGT GCT CAC TGT TTT TTC TTT GGG CGG TAG CCA ATA ACC TTA ACG ACA TTT TAT TA TCA AGG CGC ACT CCC GTT CTG G-3') and SEQ ID NO: 15 (5'-CAG CAT GGA GGC GAG AGT GAT AAA GTC TGC GCC AAC GTG GCC GAT GGT CAG AAC CCC CAG GGT TAT TGT CTC ATG AGC G-3'). The phage λ red recombinase method was used to integrate the cassette as described in Example 1. The cassette was integrated in the fuc locus on the chromosome between the fucP and fucI genes and disrupted these. The sequence of the cloning site on the chromosome is given by SEQ ID NO: 16. This sequence includes the chromosomal DNA sequences directly upstream and downstream of the cassette. The cassette is found between position 5148 and 9112.

Mutants with defects in the fuc locus are not able to grow on L-fucose as a carbon source and will form pale colonies on MacConkey medium containing 1% fucose (contrary to wild type cells which will form red colonies, as described by Albermann et al. 2010). After selection on agar plates containing chloramphenicol, the positive colonies were further tested on MacConkey medium with 1% fucose. The fucose negative colonies were further tested with by PCR using primers SEQ ID NO: 17 (GGC CTA TTT CCC TAA AGG GTT TAT TGA G) for the 5'-test and SEQ ID NO 18 (GACGATACACTTTGGTCTCTTCAACGTTG) for the 3'-test. The chloramphenicol resistance was removed by expressing a flippase as described in Example 1, thus creating the strain E. coli BW25113 ΔpheAtyrA ΔtyrR fuc::P$_{tac}$aroBaroG$^{fbr}$. Transformation of the plasmid construct pJF119ubiChbdBCD described in Example 1 then yielded the strain E. coli BW25113 ΔpheAtyrA ΔtyrR fuc::P$_{tac}$aroBaroG$^{fbr}$ pJF119ubiChbdBCD. A shake flask fermentation with IPTG induction was performed as described in Example 1. A phenol concentration of 1.2 mM was measured by HPLC after 24 hours. The HPLC method described in Example 1 was used. The phenol peaks in the samples had identical retention times and UV-spectra to a phenol standard solution (see FIG. 9).

Example 6

Phenol Production by Fermentation Using a Raw Sugar Cane Juice Containing a High Proportion of Kestose Fermentations with the strain E. coli BW25113 ΔtyrR ΔpheAtyrA pJF119ubiChbdBCD in shake flasks and in a bioreactor were performed using raw sugar cane juice as the sole energy and carbon source. The sugar cane juice was extracted from a transgenic sugar cane plant containing a high proportion of 1-kestose as well as sucrose, fructose, glucose and nystose. The concentrations of these sugars in the sugar cane juice had been measured by HPLC and had the following concentrations; glucose 14 g/l, fructose 24 g/l, sucrose 130 g/l, kestose 119 g/l, nystose 5 g/l. Further compounds in the sugar cane juice were not analysed. The juice was then used as energy and carbon source in the Riesenberg medium described in Example 1 instead of glucose. The sugar cane juice was added to yield a total sugar concentration of 15 g/l in the final medium. Thus the medium for the shake flask fermentation was given as follows; 13.3 g/L KH$_2$PO$_4$, 4 g/L (NH$_4$)$_2$PO$_4$, 1.7 g/L citrate, 2.5 g/l Luria Broth, 0.051 l/l sugar cane juice, 0.024 g/L L-phenylalanine, 0.016 g/L L-tyrosine, 10 ml/l trace element solution, 0.6 g/L MgSO$_4$*7 H$_2$O, 0.2 mM CaCl$_2$*2 H$_2$O, 0.1 g/l ampicillin. The medium used for fermentation in the bioreactor was given as follows; 15.5 g/L KH$_2$PO$_4$, 4.67 g/L (NH$_4$)$_2$PO$_4$, 1.98 g/L Citrate, 0.051 l/l sugar cane juice, 0.5 g/L Thiamine, 0.037 g/L L-Phenylalanine, 0.024 g/L L-Tyrosine, 10 ml/l trace element solution, 0.6 g/L MgSO$_4$*7 H$_2$O, 0.2 mM CaCl$_2$*2 H$_2$O, 0.1 g/l ampicillin. The trace element solution was defined in Example 1.

The fermentation in shake flasks yielded a phenol concentration of 3.1 mM after complete depletion of all sugars while the fermentation in the bioreactor yielded a phenol concentration of 0.9 mM after depletion of all sugars. These results demonstrate that it is possible to produce phenol from raw sugar juice containing a mixture of sugars including a high proportion of 1-kestose. The chromatograms of the phenol HPLC-measurement and the UV spectra of the fermentation in shake flask are given in FIG. 10.

TABLE 1

| Strain | Plasmid | Gene | Resistance |
|---|---|---|---|
| E. coli BW25113 | ΔtyrRpheAtyrA pJF119 | aroB | amp, chromosomal kan + CAT |
| E. coli BW25113 | ΔtyrRpheAtyrA pJF119 | aroGfbr | amp chromosomal kan + CAT |
| E. coli BW25113 | ΔtyrRpheAtyrA pJF119 | aroL | amp, chromosomal kan + CAT |
| E. coli BW25113 | ΔtyrRpheAtyrA pJF119 | ubiC | amp, chromosomal kan + CAT |
| E. coli BW25113 | ΔtyrRpheAtyrA pUC19 | hbdBCD | amp, chromosomal kan + CAT |
| E. coli BW25113 | ΔtyrRpheAtyrA pJF119 | aroBaroL | amp, chromosomal kan + CAT |
| E. coli BW25113 | ΔtyrRpheAtyrA pJF119 | aroLaroB | amp, chromosomal kan + CAT |
| E. coli BW25113 | ΔtyrRpheAtyrA pJF119 | aroLubiC | amp, chromosomal kan + CAT |
| E. coli BW25113 | ΔtyrRpheAtyrA pJF119 | ubiCaroB | amp, chromosomal kan + CAT |
| E. coli BW25113 | ΔtyrRpheAtyrA pJF119 | ubiCaroL | amp, chromosomal kan + CAT |
| E. coli BW25113 | ΔtyrRpheAtyrA pJF119 | aroGfbr aroL | amp, chromosomal kan + CAT |
| E. coli BW25113 | ΔtyrRpheAtyrA pJF119 | aroGfbr ubiC | amp, chromosomal kan + CAT |
| E. coli BW25113 | ΔtyrRpheAtyrA pJF119 | aroLubiCaroB | amp, chromosomal kan + CAT |
| E. coli BW25113 | ΔtyrRpheAtyrA pJF119 | aroGfbr aroLaroB | amp, chromosomal kan + CAT |
| E. coli BW25113 | ΔtyrRpheAtyrA pJF119 | a roGfbr aroLubiC | amp, chromosomal kan + CAT |
| E. coli BW25113 | ΔtyrRpheAtyrA pJF119 | aroLubiCaroBaroGfbr | amp, chromosomal kan + CAT |
| E. coli BW25113 | ΔtyrRpheAtyrA pJF119 | ubiChbdBCD | amp, chromosomal kan + CAT or kan only |
| E. coli BW25113 | ΔtyrRpheAtyrA pJF119 | aroLubiChbdBCD | amp, chromosomal kan + CAT or kan only |
| E. coli BW25113 | ΔtyrRpheAtyrA pJF119 | aroLubiChbdBCD | amp, chromosomal kan + CAT or kan only |
| E. coli BW25113 | ΔtyrRpheAtyrA pJF119 | ubiCaroLhbdBCD | amp, chromosomal kan + CAT or kan only |
| E. coli BW25113 | ΔtyrRpheAtyrA pJF119 | ubiCaroLhbdBCD | amp, chromosomal kan + CAT or kan only |
| E. coli BW25113 | ΔtyrRpheAtyrA pJF119 | aroLubiCaroBhbdBCD | amp, chromosomal kan + CAT or kan only |
| E. coli BW25113 | ΔtyrRpheAtyrA pACYC | hbdBCD | CAT |
| E. coli BW25113 | ΔtyrRpheAtyrA pACYC /pJF119 | pJF119ubiC, pACYChbdBCD | CAT |
| E. coli BW25113 | ΔtyrRpheAtyrA pACYC /pJF119 | pJF119aroLubiC, pACYChbdBCD | CAT |
| E. coli BW25113 | ΔtyrRpheAtyrA pACYC /pJF119 | pJF119ubiCaroL, pACYChbdBCD | CAT |
| E. coli BW25113 | ΔtyrRpheAtyrA pJF119 | aroLubiCaroBaroGfbr hbdBCD | amp, chromosomal kan + CAT |

TABLE 2

| Strain | Fermentation device | Conc. Phenol [mM] measured by HPLC-UV | Detection of phenol by HPLC_MS | Experiment |
|---|---|---|---|---|
| E. coli BW25113 ΔpheAtyrAΔtyrR pJF119Δ | Shake flask | below detection limit | no | Example 1, 2, 3 |

TABLE 2-continued

| Strain | Fermentation device | Conc. Phenol [mM] measured by HPLC-UV | Detection of phenol by HPLC_MS | Experiment |
|---|---|---|---|---|
| E. coli BW25113 ΔpheAtyrAΔtyrR pUC19hbdBCD | Shake flask | below detection limit | Not measured | Example 1, 2, 3 |
| E. coli BW25113 ΔpheAtyrAΔtyrR pJF119ubiChbdBCD | Shake flask | 1.44 | yes | Example 1 |
| E. coli BW25113 ΔpheAtyrAΔtyrR pJF119ubiChbdBCD | Fermenter | 4.9 | yes | Example 1 |
| E. coli BW25113 ΔpheAtyrAΔtyrR pJF119aroLubiChbdBCD | Shake flask | 0.59 | yes | Example 2 |
| E. coli BW25113 ΔpheAtyrAΔtyrR pACYChbdBCD pJF119ubiC | Fermenter | 2.3 | yes | Example 3 |
| E. coli BW25113 ΔpheAtyrAΔtyrR pJF119hbdBCDubiC | Shake flask | 0.093 | Not measured | Example 4 |
| E. coli BW25113 ΔpheAtyrAΔtyrR fuc::P$_{tac}$-aroBaroG$^{fbr}$ pJF119ubiChbdBCD | Shake flask | 1.2 | Not measured | Example 5 |
| E. coli BW25113 ΔpheAtyrAΔtyrR pACYChbdBCD pJF119ubiC | Shake flask with sugar cane juice | 3.1 | Not measured | Example 6 |
| E. coli BW25113 ΔpheAtyrAΔtyrR pACYChbdBCD pJF119ubiC | Fermenter with sugar cane juice | 0.9 | Not measured | Example 6 |

"No" signifies that the concentration is below 1 mg/l.
"Yes" signifies that the concentration is above 1 mg/l

The invention claimed is:

1. A method of generating a recombinant host strain for producing phenol, comprising the steps of
   a) providing a host comprising chorismate,
   b) transforming said host with a first nucleic acid sequence comprising ubiC (SEQ ID NO: 1) encoding chorismate lyase, and
   c) transforming said host with a second nucleic acid sequence encoding an oxygen-tolerant 4-hydroxybenzoate decarboxylase, thereby generating a recombinant host that is capable of producing phenol under aerobic conditions,
   wherein step b) and step c) are carried out simultaneously or sequentially.

2. The method according to claim 1, wherein said second nucleic acid sequence comprises hbdBCD (SEQ ID NO:2).

3. The method according to claim 1, wherein the host of step a) is overproducing chorismate, wherein said host optionally comprises one or more genetic modifications to overproduce chorismate.

4. The method according to claim 3, wherein said genetic modification comprises a deletion of one or more of tyrR, pheA and tyrA.

5. The method according to claim 3, wherein said genetic modification comprises a transformation with one or more of aroG (SEQ ID NO: 9), aroG$^{fbr}$ (SEQ ID NO: 10), aroB (SEQ ID NO: 11) and aroL (SEQ ID NO: 12).

6. The method according to claim 3, wherein said genetic modification comprises a deletion of one or more of tyrR, pheA and tyrA; and further comprises
   a transformation with one or more of aroG (SEQ ID NO: 9), aroG$^{fbr}$ (SEQ ID NO: 10), aroB (SEQ ID NO: 11) and aroL (SEQ ID NO: 12).

7. The method according to claim 1, wherein said host is selected from the group consisting of bacteria, yeast and fungi.

8. The method according to claim 1, wherein said host is a phenol-resistant host.

9. The method of claim 1, wherein the transformation in steps b) and c) comprise plasmid transformation and/or chromosomal transformation.

10. A recombinant host strain obtainable by the method of claim 1.

11. A recombinant host strain comprising chorismate and further comprising a first nucleic acid sequence comprising ubiC (SEQ ID NO: 1) and a second nucleic acid sequence encoding an oxygen-tolerant 4-hydroxybenzoate decarboxylase, wherein the recombinant strain is capable of producing phenol under aerobic conditions.

12. The recombinant host strain of claim 11, wherein said second nucleic acid sequence comprises hbdBCD (SEQ ID NO: 2).

13. The recombinant host strain of claim 1, wherein said host strain is overproducing chorismate, wherein said host strain optionally comprises one or more genetic modifications to overproduce chorismate.

14. The recombinant host strain of claim 13, wherein said genetic modification comprises a transformation with one or more of aroG (SEQ ID NO: 9), aroG$^{fbr}$ (SEQ ID NO: 10), aroB (SEQ ID NO: 11) and aroL (SEQ ID NO:12).

15. The recombinant strain of claim 13, wherein said genetic modification comprises a deletion of one or more of tyrR, pheA and tyrA; and further comprises
   a transformation with one or more of aroG (SEQ ID NO: 9), aroG$^{fbr}$ (SEQ ID NO: 10), aroB (SEQ ID NO: 11) and aroL (SEQ ID NO: 12).

16. The recombinant strain of one or more of claim 13, wherein said host is selected from the group consisting of bacteria, yeast and fungi.

17. The recombinant strain of claim 13, wherein said host is a phenol-resistant host.

18. A method of producing phenol in a recombinant host comprising the steps of
   a) providing a recombinant host strain according to claim 10, and
   b) incubating said recombinant host strain under fermentation conditions thereby producing phenol.

19. The method of claim 18, wherein phenol production is induced, and wherein the produced phenol optionally is harvested in a further step c) of harvesting the phenol from the recombinant host strain, and wherein optionally at least step b) is performed as a batch fermentation, as a fed-batch fermentation or as a continuous fermentation.

20. The method of claim 18, wherein said fermentation conditions comprise aerobic conditions.

21. The method of claim 18, wherein said fermentation conditions comprise the presence of a raw sugar cane juice, wherein said raw sugar cane juice optionally comprises a high concentration of 1-kestose.

22. A method of producing phenol in a recombinant host comprising the steps of
   a) providing a recombinant host strain according to claim 11, and
   b) incubating said recombinant host strain under fermentation conditions thereby producing phenol.

* * * * *